(12) United States Patent
Müller et al.

(10) Patent No.: US 7,300,908 B2
(45) Date of Patent: Nov. 27, 2007

(54) FUNGICIDAL TRIAZOLOPYRIMIDINES, METHOD FOR THE PRODUCTION THEREOF AND USE THEREOF IN CONTROLLING NOXIOUS FUNGI AND AGENTS CONTAINING SAID COMPOUNDS

(75) Inventors: Bernd Müller, Frankenthal (DE); Hubert Sauter, Mannheim (DE); Markus Gewehr, Kastellaun (DE); Wassilios Grammenos, Ludwigshafen (DE); Jordi Tormo i Blasco, Limburgerhof (DE); Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Frank Schieweck, Hessheim (DE); Michael Rack, Heidelberg (DE); Gisela Lorenz, Hambach (DE); Siegfried Strathmann, Limburgerhof (DE); Eberhard Ammermann, Heppenheim (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 108 days.

(21) Appl. No.: 10/482,216

(22) PCT Filed: Jul. 3, 2002

(86) PCT No.: PCT/EP02/07340

§ 371 (c)(1),
(2), (4) Date: Aug. 11, 2004

(87) PCT Pub. No.: WO03/004465

PCT Pub. Date: Jan. 16, 2003

(65) Prior Publication Data

US 2005/0090665 A1 Apr. 28, 2005

(30) Foreign Application Priority Data

Jul. 5, 2001 (DE) ................ 101 32 059

(51) Int. Cl.
*C07D 487/04* (2006.01)
*A01N 43/48* (2006.01)

(52) U.S. Cl. ............ 504/241; 544/263
(58) Field of Classification Search ......... 514/259.31; 544/263; 564/335, 412; 504/241
See application file for complete search history.

(56) References Cited

U.S. PATENT DOCUMENTS 2,388,579 A * 11/1945 Smith et al. ......... 549/462
2,443,136 A * 6/1948 Heimbach .......... 544/263
4,567,263 A   1/1986 Eicken et al. ........ 544/263
6,057,456 A * 5/2000 Hartwig et al. ....... 548/540

FOREIGN PATENT DOCUMENTS

| EP | 071 792 | 2/1983 |
|---|---|---|
| EP | 550 113 | 7/1993 |
| EP | 770 615 | 5/1997 |
| EP | 834 513 | 4/1998 |
| EP | 048 649 | 11/2000 |
| EP | 1048649 A1 * | 11/2000 |
| WO | WO 9414809 A1 * | 7/1994 |
| WO | 94/20501 | 9/1994 |
| WO | 98/46608 | 10/1998 |
| WO | 99/41255 | 8/1999 |

OTHER PUBLICATIONS

Misiti, Domenico; Settimj, Guido; Mantovani, Piero; Chiavarelli, Stefano, Annali dell'Istituto Superiore di Sanita, 4(5-6), 521-33 (Italian) 1968.*
J.Chem.Sco.,1961, 1311-1321, XP009004205.

* cited by examiner

*Primary Examiner*—Brenda L. Coleman
*Assistant Examiner*—Suslanna Moore
(74) *Attorney, Agent, or Firm*—Novak Druce & Quigg, LLP

(57) ABSTRACT

Triazolopyrimidines of formula (I), wherein the index and substituents have the following meaning: n=0 or a whole number of 1-5; R=halogen, cyano, hydroxy, cyanate, alkyl, alkenyl, alkinyl, halogenalkyl, halogenalkenyl, alkoxy, alkenyloxy, alkinyloxy, halogenalkoxy, cycloalkyl, cycloalkenyl, cycloalkoxy, alkoxycarbonyl, alkenyloxycarbonyl, alkinyloxycarbonyl, aminocarbonyl, alkylaminocarbonyl, dialkylaminocarbonyl, alkoximinoalkyl, alkenyloximinocarbonyl, alkinyloximinoalkyl, alkylcarbonyl, alkenylcarbonyl, alkinylcarbonyl, cycloalkylcarbonyl or a five to ten membered saturated, partially unsaturated or aromatic heterocycle, containing one to four heteroatoms from the group O, N or S; $R^1$=alkyl, alkenyl, alkinyl, cycloalkyl, cycloalkenyl, phenyl, naphthyl or a five to ten membered saturated, partially unsaturated or aromatic heterocycle, containing one to four heteroatoms from the group O, N or S, R and/or $R^1$ being able to be substituted according to the description; $R^2$=alkyl, alkenyl or alkinyl which can be substituted by halogen, cyano, nitro, alkoxy or alkoxycarbonyl. The invention also relates to a method for the production of said compounds, agents containing same, and the use thereof in controlling noxious fungi

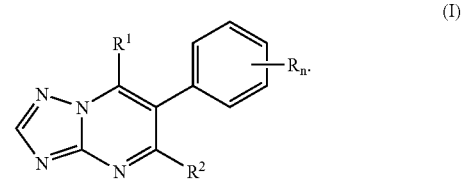

10 Claims, No Drawings

FUNGICIDAL TRIAZOLOPYRIMIDINES, METHOD FOR THE PRODUCTION THEREOF AND USE THEREOF IN CONTROLLING NOXIOUS FUNGI AND AGENTS CONTAINING SAID COMPOUNDS

The present invention relates to triazolopyrimidines of the formula I

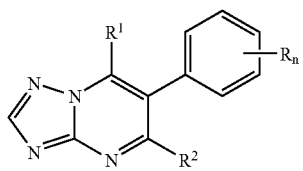

I in which the index and the substituents are as defined below:
n is 0 or an integer from 1 to 5;
R is halogen, cyano, hydroxy, cyanato (OCN), $C_1$-$C_8$-alkyl, $C_2$-$C_{10}$-alkenyl, $C_2$-$C_{10}$-alkynyl, $C_1$-$C_6$-haloalkyl, $C_2$-$C_{10}$-haloalkenyl, $C_1$-$C_6$-alkoxy, $C_2$-$C_{10}$-alkenyloxy, $C_2$-$C_{10}$-alkynyloxy, $C_1$-$C_6$-haloalkoxy, $C_3$-$C_6$-cycloalkyl, $C_3$-$C_6$-cycloalkenyl, $C_3$-$C_6$-cycloalkoxy, $C_1$-$C_8$-alkoxycarbonyl, $C_2$-$C_{10}$-alkenyloxycarbonyl, $C_2$-$C_{10}$-alkynyloxycarbonyl, aminocarbonyl, $C_1$-$C_8$-alkylaminocarbonyl, di-($C_1$-$C_8$)alkylaminocarbonyl, $C_1$-$C_8$-alkoximinoalkyl, $C_2$-$C_{10}$-alkenyloximinocarbonyl, $C_2$-$C_{10}$-alkynyloximinoalkyl, $C_1$-$C_8$-alkylcarbonyl, $C_2$-$C_{10}$-alkenylcarbonyl, $C_2$-$C_{10}$-alkynylcarbonyl, $C_3$-$C_6$-cycloalkylcarbonyl, or a five- to ten-membered saturated, partially unsaturated or aromatic heterocycle which contains one to four heteroatoms from the group consisting of O, N and S;
$R^1$ is $C_1$-$C_{10}$-alkyl, $C_2$-$C_{10}$-alkenyl, $C_2$-$C_{10}$-alkynyl, $C_3$-$C_{12}$-cycloalkyl, $C_3$-$C_{10}$-cycloalkenyl, phenyl, naphthyl or a five- to ten-membered saturated, partially unsaturated or aromatic heterocycle which contains one to four heteroatoms from the group consisting of O, N and S, where R and/or $R^1$ may be partially or fully halogenated or may be substituted by one to four identical or different groups $R^a$:
$R^a$ is halogen, cyano, nitro, hydroxyl, $C_1$-$C_6$-alkyl, $C_1$-$C_6$-haloalkyl, $C_1$-$C_6$-alkylcarbonyl, $C_3$-$C_6$-cycloalkyl, $C_1$-$C_6$-alkoxy, $C_1$-$C_6$-haloalkoxy, $C_1$-$C_6$-alkoxycarbonyl, $C_3$-$C_6$-alkylthio, $C_1$-$C_6$-alkylamino, di-$C_1$-$C_6$-alkylamino, $C_2$-$C_6$-alkenyl, $C_2$-$C_6$-alkenyloxy, $C_3$-$C_6$-alkynyloxy, $C_3$-$C_6$-cycloalkyl, $C_1$-$C_8$-alkoximino, $C_2$-$C_{10}$-alkenyloximino, $C_2$-$C_{10}$-alkynyloximino, aryl-$C_1$-$C_8$-alkyloximino, $C_2$-$C_{10}$-alkynyl, $C_2$-$C_{10}$-alkenyloxycarbonyl, $C_2$-$C_{10}$-alkynyloxycarbonyl, phenyl, naphthyl, a five- to ten-membered saturated, partially unsaturated or aromatic heterocycle which contains one to four heteroatoms from the group consisting of O, N and S,
where these aliphatic, alicyclic or aromatic groups for their part may be partially or fully halogenated or may carry one to three groups $R^b$:
$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;
and/or one to three of the following radicals:
cycloalkyl, cycloalkoxy, heterocyclyl, heterocyclyloxy, where the cyclic systems contain 3 to 10 ring members; aryl, aryloxy, arylthio, aryl-$C_1$-$C_6$-alkoxy, aryl-$C_1$-$C_6$-alkyl, hetaryl, hetaryloxy, hetarylthio, where the aryl radicals preferably contain 6 to 10 ring members and the hetaryl radicals 5 or 6 ring members, where the cyclic systems may be partially or fully halogenated or substituted by alkyl or haloalkyl groups; and
$R^2$ is $C_1$-$C_4$-alkyl, $C_2$-$C_4$-alkenyl or $C_2$-$C_4$-alkynyl, which may be substituted by halogen, cyano, nitro, $C_1$-$C_2$-alkoxy, or $C_1$-$C_4$-alkoxycarbonyl.

Moreover, the invention relates to a process for preparing these compounds, to compositions comprising them and to their use for controlling harmful fungi.

5-chlorotriazolopyrimidines for controlling harmful fungi are disclosed in EP-A 71 792, EP-A 550 113, WO-A 94/20501, EP-A 834 513, WO-A 98/46608 and WO-A 99/41255.

However, in many cases, their activity is unsatisfactory.

It is an object of the invention, to provide compounds having improved activity.

We have found that this object is achieved by the compounds defined at the outset. Furthermore, we have found a process for their preparation, compositions comprising them and methods for controlling harmful fungi using the compounds I.

The compounds of the formula I differ from the compounds in the abovementioned publications in that the 5-alkyl radical is combined with groups in position 7 which are attached via carbon.

Compared to the known compounds, the compounds of the formula I have increased activity against harmful fungi.

The compounds I can be obtained by different routes; advantageously, 5-aminotriazole of the formula II is used as starting material and condensed with dicarbonyl compounds of the formula III.

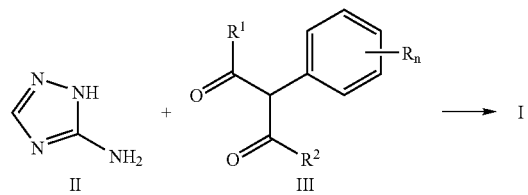

This reaction usually takes place at temperatures of from 80° C. to 250° C., preferably from 120° C. to 180° C., in the absence of a solvent or in an inert organic solvent in the presence of a base [cf. EP-A 770 615] or in the presence of acetic acid under the conditions known from Adv. Het. Chem. 57 (1993), 81 ff.

Suitable solvents are aliphatic hydrocarbons, aromatic hydrocarbons such as toluene, o-, m- and p-xylene, halogenated hydrocarbons, ethers, nitriles, ketones, alcohols, and also N-methylpyrrolidone, dimethyl sulfoxide, dimethylformamide and dimethylacetamide. The reaction is particularly preferably carried out in the absence of a solvent or in chlorobenzene, xylene, dimethyl sulfoxide or N-methylpyrrolidone. It is also possible to use mixtures of the solvents mentioned.

Suitable bases are, in general, inorganic compounds, such as alkali metal and alkaline earth metal hydroxides, alkali metal and alkaline earth metal oxides, alkali metal and alkaline earth metal hydrides, alkali metal amides, alkali metal and alkaline earth metal carbonates and also alkali metal bicarbonates, organometallic compounds, in particular alkali metal alkyls, alkylmagnesium halides and also alkali metal and alkaline earth metal alkoxides and dimethoxymagnesium, moreover organic bases, for example tertiary amines, such as trimethylamine, triethylamine, triisopropylamine, tributylamine and N-methylpiperidine, N-methylmorpholine, pyridine, substituted pyridines, such as collidine, lutidine and 4-dimethylaminopyridine, and also bicyclic amines. Particular preference is given to tertiary amines such as triisopropylamine, tributylamine, N-methylmorpholine or N-methylpiperidine.

The bases are generally employed in catalytic amounts; however, they can also be employed in equimolar amounts, in excess or, if appropriate, as solvent.

The starting materials are generally reacted with one another in equimolar amounts. In terms of yield, it may be advantageous to employ an excess of base and diketone III, based on II.

The compounds of the formula I' according to the invention can also be obtained by reacting 5-halotriazolopyrimidines of the formula IV with substituted malonic acid esters of the formula V, where $R^X$ is $C_1$-$C_4$-alkyl, allyl, phenyl or benzyl, followed by hydrolysis of the resulting ester VI and decarboxylation of the carboxylic acid VIa.

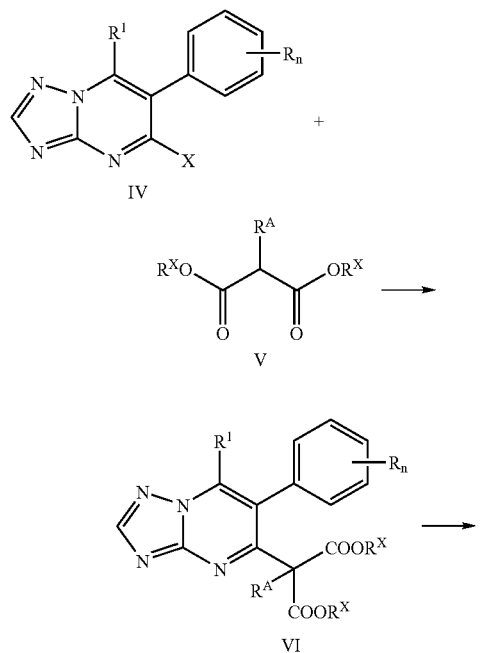

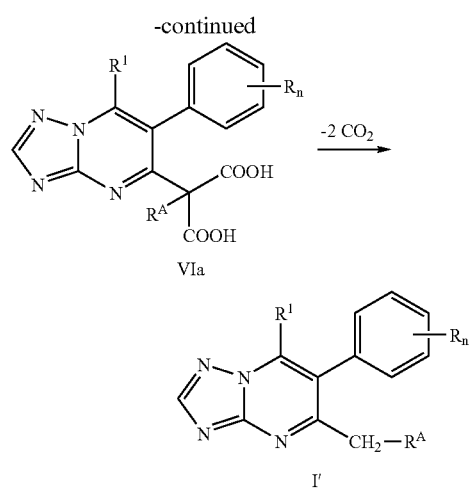

In the formula IV, X is halogen, in particular chlorine or bromine. The compounds IV are known from the publications cited at the outset. In the formula I', n, R and $R^1$ have the definitions given for the formula I and $R^4$ is hydrogen or $C_1$-$C_3$-alkyl which may be substituted by halogen, cyano, nitro or $C_1$-$C_2$-alkoxy.

In a preferred embodiment of the process according to the invention, $R^4$ is hydrogen or methyl, in particular hydrogen.

The starting materials V are known from the literature [J. Am. Chem. Soc. 64 (1942), 2714: J. Org. Chem. 39 (1974), 2172; Helv. Chim. Acta 61 (1978), 1565], or they can be prepared according to the literature cited.

The subsequent hydrolysis of the ester is carried out under generally known conditions [cf.: Greene & Wuts, Protective Groups in Organic Synthesis, Wiley (1991), p. 224 ff.: cleavage of alkyl esters under Pd catalysis (p. 248); reductive cleavage of benzyl esters (p. 251); cleavage of methyl or ethyl esters in the presence of lithium salts such as Liu (p. 232). LiBr or LiCl; or under acidic or alkaline conditions]. Depending on the structural elements $R^4$, $R_n$ and $R^1$, alkaline or acidic hydrolysis of the compounds VI may be advantageous. It is possible that full or partial decarboxylation to I' takes place even under the conditions of ester hydrolysis.

The decarboxylation is usually carried out at temperatures of from 20° C. to 180° C., preferably from 50° C. to 120° C., in an inert solvent, if appropriate in the presence of an acid.

Suitable acids are hydrochloric acid, sulfuric acid, phosphoric acid, formic acid, acetic acid, p-toluenesulfonic acid. Suitable solvents are water, aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also dimethyl sulfoxide, dimethylformamide and dimethylacetamide; the reaction is particularly preferably carried out in hydrochloric acid or acetic acid. It is also possible to use mixtures of the solvents mentioned.

Compounds of the formula I can also be obtained by coupling 5-halotriazolopyrimidines of the formula IV with organometallic reagents of the formula VII. In one embodiment of this process, the reaction is carried out under transition metal catalysis, such as Ni or Pd catalysis.

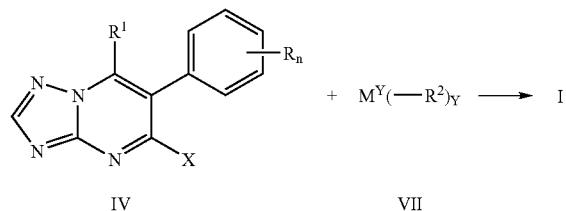

In the formula VII, M is a metal ion having the valency Y, such as, for example, B, Zn or Sn. This reaction can be carried out, for example, similarly to the following methods: J. Chem. Soc. Perkin Trans. 1 (1994), 1187, ibid 1 (1996), 2345; WO-A 99/41255; Aust. J. Chem. 43 (1990), 733; J. Org. Chem. 43 (1978), 358; J. Chem. Soc. Chem. Commun. (1979). 866; Tetrahedron Lett. 34 (1993), 8267; ibid 33 (1992), 413.

The reaction mixtures are worked up in a customary manner, for example by mixing with water, phase separation and, if required, chromatographic purification of the crude products. Some of the intermediates and end products are obtained in the form of colorless or slightly brownish, viscous oils, which are purified or freed from volatile components under reduced pressure and at moderately elevated temperatures. If the intermediates and end products are obtained as solids, purification can also be carried out by recrystallization or digestion.

If individual compounds I cannot be obtained by the routes described above, they can be prepared by derivatization of other compounds I.

If the synthesis yields isomer mixtures, a separation is generally not necessarily required since in some cases the individual isomers can be converted into one another during the preparation for use or upon use (for example under the action of light, acids or bases). Similar conversions may also occur after use, for example in the treatment of plants in the treated plant or in the harmful fungus or animal pest to be controlled.

In the definitions of the symbols given in the above formulae, collective terms were used which generally represent the following substituents:

Halogen: fluorine, chlorine, bromine and iodine;

Alkyl: saturated, straight-chain or branched hydrocarbon radicals having 1 to 4, 6, 8 or 10 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 10 carbon atoms (as mentioned above), where all or some of the hydrogen atoms in these groups may be replaced by halogen atoms as mentioned above, for example $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkenyl: unsaturated, straight-chain or branched hydrocarbon radicals having 2 to 4, 6, 8 or 10 carbon atoms and a double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl. 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Haloalkenyl: unsaturated, straight-chain or branched hydrocarbon radicals having 2 to 10 carbon atoms and a double bond in any position (as mentioned above), where all or some of the hydrogen atoms in these groups may be replaced by halogen atoms as mentioned above, in particular by fluorine, chlorine and bromine;

Alkynyl: straight-chain or branched hydrocarbon groups having 2 to 4, 6, 8 or 10 carbon atoms and a triple bond in any position, for example $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Cycloalkyl: mono- or bicyclic, saturated hydrocarbon groups having 3 to 6, 8, 10 or 12 carbon ring members, for example $C_3$-$C_8$-cycloalkyl such as cyclopropyl, cyclobutyl, cyclopentyl, cyclohexyl, cycloheptyl and cyclooctyl, or $C_7$-$C_{12}$-bicycloalkyl;

Aryl: a mono- to trinuclear aromatic ring system having 6 to 14 carbon ring members, for example phenyl, naphthyl and anthracenyl;

Five- to ten-membered saturated, partially unsaturated or aromatic heterocycle which contains one to four heteroatoms from the group consisting of O, N and S:

5- or 6-membered heterocyclyl which contains one to three nitrogen atoms and/or one oxygen or sulfur atom or one or two oxygen and/or sulfur atoms, for example 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydro-triazin-2-yl and 1,2,4-hexahydrotriazin-3-yl;

5-membered heteroaryl which contains one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

Benzo-fused 5-membered heteroaryl which contains one to three nitrogen atoms or one nitrogen atom and one oxygen or sulfur atom: 5-membered heteroaryl groups which, in addition to carbon atoms, may contain one to four nitrogen atoms or one to three nitrogen atoms and one sulfur or oxygen atom as ring members and in which two adjacent carbon ring members or a nitrogen and an adjacent carbon ring member may be bridged by a buta-1,3-diene-1,4-diyl group;

6-membered heteroaryl which contains one to three or one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Alkylene: divalent unbranched chains of 3 to 5 $CH_2$ groups, for example $CH_2$, $CH_2CH_2$, $CH_2CH_2CH_2$, $CH_2CH_2CH_2CH_2$ and $CH_2CH_2CH_2CH_2CH_2$;

Oxyalkylene: divalent unbranched chains of 2 to 4 $CH_2$ groups, where one valency is attached to the skeleton via an oxygen atom, for example $OCH_2CH_2$, $OCH_2CH_2CH_2$ and $OCH_2CH_2CH_2CH_2$;

Oxyalkyleneoxy: divalent unbranched chains of 1 to 3 $CH_2$ groups, where both valencies are attached to the skeleton via an oxygen atom, for example $OCH_2O$, $OCH_2CH_2O$ and $OCH_2CH_2CH_2O$.

The scope of the present invention includes the (R) and (S) isomers and the racemates of compounds of the formula I having chiral centers.

With a view to the intended use of the triazolopyrimidines of the formula I, the following meanings of the substituents are particularly preferred, in each case on their own or in combination:

Preference is given to compounds I in which $R^1$ is $C_3$-$C_8$-alkyl, $C_3$-$C_8$-alkenyl, $C_3$-$C_8$-alkynyl, $C_3$-$C_6$-cycloalkyl or $C_5$-$C_6$-cycloalkenyl.

Particular preference is given to compounds I in which $R^1$ is $C_1$-$C_6$-alkyl or $C_1$-$C_6$-haloalkyl.

In addition, preference is given to compounds I in which $R^1$ is $C_2$-$C_{10}$-alkenyl or $C_2$-$C_{10}$-alkynyl.

Likewise, preference is given to compounds I in which $R^1$ is a 5- or 6-membered saturated or aromatic heterocycle.

Moreover, particular preference is given to compounds I in which $R^1$ is $C_3$-$C_6$-cycloalkyl which may be substituted by $C_1$-$C_4$-alkyl.

Particular preference is given to compounds I in which $R^a$ is halogen, cyano, $C_1$-$C_6$-alkyl, $C_2$-$C_6$-alkenyl, $C_2$-$C_6$-alkynyl, $C_1$-$C_6$-alkoxy, $C_1$-$C_6$-alkoxycarbonyl, $C_1$-$C_6$-alkoximino, $C_2$-$C_6$-alkenyloximino or $C_2$-$C_6$-alkynyloximino.

Particular preference is given to compounds I in which $R^b$ is halogen, cyano, $C_1$-$C_6$-alkyl, $C_2$-$C_6$-alkenyl, $C_2$-$C_6$-alkynyl or $C_1$-$C_6$-alkoxy.

Particular preference is also given to compounds I in which $R^2$ is $C_1$-$C_4$-alkyl which may be substituted by halogen.

Likewise, particular preference is given to compounds I in which $R^2$ is methyl.

In addition, particular preference is given to compounds I in which $R^2$ is halomethyl.

Particular preference is also given to compounds I in which one substituent R is in the 2-position and n is an integer from 1 to 4, in particular 1 to 3.

Moreover, particular preference is given to compounds I in which n is 2 or 3 and one substituent R is in the 2-position.

Furthermore, preference is given to compounds I in which R is fluorine, chlorine, bromine, cyano, $C_1$-$C_6$-alkyl, $C_1$-$C_6$-alkoxy, $C_1$-$C_6$-alkoxycarbonyl, $C_1$-$C_6$-alkylcarbonyl, $C_1$-$C_6$-alkoximino-$C_1$-$C_6$-alkyl, $C_1$-$C_6$-alkenyloximino-$C_1$-$C_6$-alkyl, or $C_1$-$C_6$-alkynyloximino-$C_1$-$C_6$-alkyl.

Likewise, particular preference is given to compounds I in which R is fluorine, chlorine, methyl, trifluoromethyl or methoxy.

In addition, particular preference is given to compounds I in which $R_n$ is 2-chloro, 2-fluoro, 2,6-difluoro, 2-methoxy, 2-trifluoromethyl, 2-trifluoromethyl-6-chloro, 2-chloro-6-fluoro, 2,4,6-trifluoro, 2,6-difluoro-4-methoxy or pentafluoro.

Very particular preference is given to compounds I in which $R_n$ is 2-chloro-6-fluoro, 2,6-difluoro-4-methoxy or 2,4,6-trifluoro.

Moreover, particular preference is given to compounds IA in which n, R and $R^1$ have the meanings given in formula I:

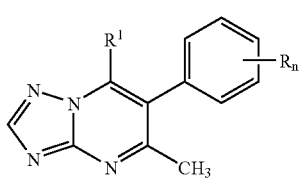

IA

With a view to their use, most particular preference is given to the compounds I compiled in the tables below. Moreover, the groups mentioned in the tables for a substituent are themselves, independently of the combination in which they are mentioned, a particularly preferred embodiment of the substituent in question.

Table 1
Compounds of the formula IA in which $R_n$ is 2-chloro and $R^1$ for each compound corresponds to one row of Table A Table 2
Compounds of the formula IA in which $R_n$ is 2-fluoro and $R^1$ for each compound corresponds to one row of Table A Table 3
Compounds of the formula IA in which $R_n$ is 2,6-difluoro and $R^1$ for each compound corresponds to one row of Table A Table 4
Compounds of the formula IA in which $R_n$ is 2-methoxy and $R^1$ for each compound corresponds to one row of Table A Table 5
Compounds of the formula IA in which $R_n$ is 2-trifluoromethyl and $R^1$ for each compound corresponds to one row of Table A Table 6
Compounds of the formula IA in which $R_n$ is 2-trifluoromethyl-6-chloro and $R^1$ for each compound corresponds to one row of Table A Table 7
Compounds of the formula IA in which $R_n$ is 2-chloro,6-fluoro and $R^1$ for each compound corresponds to one row of Table A Table 8
Compounds of the formula IA in which $R_n$ is 2,4,6-trifluoro and $R^1$ for each compound corresponds to one row of Table A Table 9
Compounds of the formula IA in which $R_n$ is 2,6-difluoro-4-methoxy and $R^1$ for each compound corresponds to one row of Table A Table 10
Compounds of the formula IA in which $R_n$ is pentafluoro and $R^1$ for each compound corresponds to one row of Table A Table 11
Compounds of the formula IA in which $R_n$ is 2-fluoro-3-methyl and $R^1$ for each compound corresponds to one row of Table A Table 12
Compounds of the formula IA, in which $R_n$ is 2-methyl and $R^1$ for each compound corresponds to one row of Table A Table 13
Compounds of the formula IA, in which $R_n$ is 2,4-dimethyl and $R^1$ for each compound corresponds to one row of Table A Table 14
Compounds of the formula IA, in which $R_n$ is 2,5-dimethyl and $R^1$ for each compound corresponds to one row of Table A Table 15
Compounds of the formula IA, in which $R_n$ is 2-methyl-4-ethyl and $R^1$ for each compound corresponds to one row of Table A Table 16
Compounds of the formula IA, in which $R_n$ is 2-methyl-4-cyano and $R^1$ for each compound corresponds to one row of Table A Table 17
Compounds of the formula IA, in which $R_n$ is 2-methyl-4-bromo and $R^1$ for each compound corresponds to one row of Table A Table 18
Compounds of the formula IA, in which $R_n$ is 2-methyl-4-chloro and $R^1$ for each compound corresponds to one row of Table A Table 19
Compounds of the formula IA, in which $R_n$ is 2-methyl-4-fluoro and $R^1$ for each compound corresponds to one row of Table A Table 20
Compounds of the formula IA, in which $R_n$ is 2-methyl-5-fluoro and $R^1$ for each compound corresponds to one row of Table A Table 21
Compounds of the formula IA, in which $R_n$ is 2-methyl-4-methoxy and $R^1$ for each compound corresponds to one row of Table A Table 22
Compounds of the formula IA, in which $R_n$ is 2-methyl-4-methoxycarbonyl and $R^1$ for each compound corresponds to one row of Table A Table 23
Compounds of the formula IA, in which $R_n$ is 2-methyl-4-ethoxycarbonyl and $R^1$ for each compound corresponds to one row of Table A Table 24
Compounds of the formula IA, in which $R_n$ is 2,5-dimethyl-4-bromo and $R^1$ for each compound corresponds to one row of Table A Table 25
Compounds of the formula IA, in which $R_n$ is 2,4-difluoro and $R^1$ for each compound corresponds to one row of Table A Table 26
Compounds of the formula IA, in which $R_n$ is 2-fluoro-4-bromo and $R^1$ for each compound corresponds to one row of Table A Table 27
Compounds of the formula IA, in which $R_n$ is 2-fluoro-4-chloro and $R^1$ for each compound corresponds to one row of Table A Table 28
Compounds of the formula IA, in which $R_n$ is 2-fluoro-4-methoxy and $R^1$ for each compound corresponds to one row of Table A Table 29
Compounds of the formula IA, in which $R_n$ is 2-fluoro-4-methyl and $R^1$ for each compound corresponds to one row of Table A Table 30
Compounds of the formula IA, in which $R_n$ is 2-fluoro-5-methyl and $R^1$ for each compound corresponds to one row of Table A Table 31
Compounds of the formula IA, in which $R_n$ is 2-fluoro-4-methoxycarbonyl and $R^1$ for each compound corresponds to one row of Table A Table 32
Compounds of the formula IA, in which $R_n$ is 2-fluoro-4-ethoxycarbonyl and $R^1$ for each compound corresponds to one row of Table A Table 33
Compounds of the formula IA, in which $R_n$ is 2-fluoro-4-ethyl and $R^1$ for each compound corresponds to one row of Table A Table 34
Compounds of the formula IA, in which $R_n$ is 2-fluoro-4-cyano and $R^1$ for each compound corresponds to one row of Table A Table 35
Compounds of the formula IA, in which $R_n$ is 2,4,5-trifluoro and $R^1$ for each compound corresponds to one row of Table A Table 36
Compounds of the formula IA, in which $R_n$ is 2,4-dichloro and $R^1$ for each compound corresponds to one row of Table A Table 37
Compounds of the formula IA, in which $R_n$ is 2-chloro-4-fluoro and $R^1$ for each compound corresponds to one row of Table A Table 38
Compounds of the formula IA, in which $R_n$ is 2-chloro-4-methoxy and $R^1$ for each compound corresponds to one row of Table A Table 39
Compounds of the formula IA, in which $R_n$ is 2-chloro-4-methyl and $R^1$ for each compound corresponds to one row of Table A Table 40
Compounds of the formula IA, in which $R_n$ is 2-chloro-4-bromo and $R^1$ for each compound corresponds to one row of Table A Table 41
Compounds of the formula IA, in which $R_n$ is 2-chloro-4-ethyl and $R^1$ for each compound corresponds to one row of Table A Table 42
Compounds of the formula IA, in which $R_n$ is 2-chloro-4-methoxycarbonyl and $R^1$ for each compound corresponds to one row of Table A Table 43
Compounds of the formula IA, in which $R_n$ is 2-chloro-4-ethoxycarbonyl and $R^1$ for each compound corresponds to one row of Table A Table 44
Compounds of the formula IA, in which $R_n$ is 2-chloro-4-cyano and $R^1$ for each compound corresponds to one row of Table A

TABLE A

| No. | $R^1$ |
|---|---|
| A-1 | $CH_3$ |
| A-2 | $CH_2CH_3$ |
| A-3 | $CH_2CH_2CH_3$ |
| A-4 | $CH(CH_3)_2$ |
| A-5 | $CH_2CH(CH_3)_2$ |
| A-6 | (±) $CH(CH_3)CH_2CH_3$ |
| A-7 | (R) $CH(CH_3)CH_2CH_3$ |
| A-8 | (S) $CH(CH_3)CH_2CH_3$ |
| A-9 | $(CH_2)_3CH_3$ |
| A-10 | $C(CH_3)_3$ |
| A-11 | $(CH_2)_4CH_3$ |
| A-12 | $CH(CH_2CH_3)_2$ |
| A-13 | $CH_2CH_2CH(CH_3)_2$ |
| A-14 | (±) $CH(CH_3)(CH_2)_2CH_3$ |
| A-15 | (R) $CH(CH_3)(CH_2)_2CH_3$ |
| A-16 | (S) $CH(CH_3)(CH_2)_2CH_3$ |
| A-17 | (±) $CH_2CH(CH_3)CH_2CH_3$ |
| A-18 | (R) $CH_2CH(CH_3)CH_2CH_3$ |
| A-19 | (S) $CH_2CH(CH_3)CH_2CH_3$ |
| A-20 | (±) $CH(CH_3)CH(CH_3)_2$ |
| A-21 | (R) $CH(CH_3)CH(CH_3)_2$ |
| A-22 | (S) $CH(CH_3)CH(CH_3)_2$ |
| A-23 | $(CH_2)_5CH_3$ |
| A-24 | (±, ±) $CH(CH_3)CH(CH_3)CH_2CH_3$ |
| A-25 | (±, R) $CH(CH_3)CH(CH_3)CH_2CH_3$ |
| A-26 | (±, S) $CH(CH_3)CH(CH_3)CH_2CH_3$ |
| A-27 | (±) $CH_2CH(CH_3)CF_3$ |
| A-28 | (R) $CH_2CH(CH_3)CF_3$ |
| A-29 | (S) $CH_2CH(CH_3)CF_3$ |
| A-30 | (±) $CH_2CH(CF_3)CH_2CH_3$ |
| A-31 | (R) $CH_2CH(CF_3)CH_2CH_3$ |
| A-32 | (S) $CH_2CH(CF_3)CH_2CH_3$ |
| A-33 | (±, ±) $CH(CH_3)CH(CH_3)CF_3$ |
| A-34 | (±, R) $CH(CH_3)CH(CH_3)CF_3$ |
| A-35 | (±, S) $CH(CH_3)CH(CH_3)CF_3$ |
| A-36 | (±, ±) $CH(CH_3)CH(CF_3)CH_2CH_3$ |
| A-37 | (±, R) $CH(CH_3)CH(CF_3)CH_2CH_3$ |
| A-38 | (±, S) $CH(CH_3)CH(CF_3)CH_2CH_3$ |

TABLE A-continued

| No. | R¹ |
|---|---|
| A-39 | $CF_3$ |
| A-40 | $CF_2CF_3$ |
| A-41 | $CF_2CF_2CF_3$ |
| A-42 | $c-C_3H_5$ |
| A-43 | $(1-CH_3)-c-C_3H_4$ |
| A-44 | $c-C_5H_9$ |
| A-45 | $c-C_6H_{11}$ |
| A-46 | $(4-CH_3)-c-C_6H_{10}$ |
| A-47 | $CH_2C(CH_3)=CH_2$ |
| A-48 | $CH_3CH_2C(CH_3)=CH_2$ |
| A-49 | $CH_2-C(CH_3)_3$ |
| A-50 | $CH_2-Si(CH_3)_3$ |
| A-51 | $n-C_6H_{13}$ |
| A-52 | $(CH_2)_3-CH(CH_3)_2$ |
| A-53 | $(CH_2)_2-CH(CH_3)-C_2H_5$ |
| A-54 | $CH_2-CH(CH_3)-n-C_3H_7$ |
| A-55 | $CH(CH_3)-n-C_4H_9$ |
| A-56 | $CH_2-CH(C_2H_5)_2$ |
| A-57 | $CH(C_2H_5)-n-C_3H_7$ |
| A-58 | $CH_2-c-C_5H_9$ |
| A-59 | $CH_2-CH(CH_3)-CH(CH_3)_2$ |
| A-60 | $CH(CH_3)-CH_2CH(CH_3)_2$ |
| A-61 | $CH(CH_3)-CH(CH_3)-C_2H_5$ |
| A-62 | $CH(CH_3)-C(CH_3)_3$ |
| A-63 | $(CH_2)_2-C(CH_3)_3$ |
| A-64 | $CH_2-C(CH_3)_2-C_2H_5$ |
| A-65 | $2-CH_3-c-C_5H_8$ |
| A-66 | $3-CH_3-c-C_5H_8$ |
| A-67 | $C(CH_3)_2-n-C_3H_7$ |
| A-68 | $(CH_2)_6-CH_3$ |
| A-69 | $(CH_2)_4-CH(CH_3)_2$ |
| A-70 | $(CH_2)_3-CH(CH_3)-C_2H_5$ |
| A-71 | $(CH_2)_2-CH(CH_3)-n-C_3H_7$ |
| A-72 | $CH_2-CH(CH_3)-n-C_4H_9$ |
| A-73 | $CH(CH_3)-n-C_5H_{11}$ |
| A-74 | $(CH_2)_3C(CH_3)_3$ |
| A-75 | $(CH_2)_2CH(CH_3)-CH(CH_3)_2$ |
| A-76 | $(CH_2)CH(CH_3)-CH_2CH(CH_3)_2$ |
| A-77 | $CH(CH_3)(CH_2)_2-CH(CH_3)_2$ |
| A-78 | $(CH_2)_2C(CH_3)_2C_2H_5$ |
| A-79 | $CH_2CH(CH_3)CH(CH_3)C_2H_5$ |
| A-80 | $CH(CH_3)CH_2CH(CH_3)C_2H_5$ |
| A-81 | $CH_2C(CH_3)_2-n-C_3H_7$ |
| A-82 | $CH(CH_3)CH(CH_3)-n-C_3H_7$ |
| A-83 | $C(CH_3)_2-n-C_4H_9$ |
| A-84 | $(CH_2)_2CH(C_2H_5)_2$ |
| A-85 | $CH_2CH(C_2H_5)-n-C_3H_7$ |
| A-86 | $CH(C_2H_5)-n-C_4H_9$ |
| A-87 | $CH_2CH(CH_3)C(CH_3)_3$ |
| A-88 | $CH(CH_3)CH_2C(CH_3)_3$ |
| A-89 | $CH_2C(CH_3)_2CH(CH_3)_2$ |
| A-90 | $CH_2C(C_2H_5)_2CH(CH_3)_2$ |
| A-91 | $CH(CH_3)CH(CH_3)CH(CH_3)_2$ |
| A-92 | $C(CH_3)_2CH_2CH(CH_3)_2$ |
| A-93 | $CH(C_2H_5)CH_2CH(CH_3)_2$ |
| A-94 | $CH(CH_3)C(CH_3)_2C_2H_5$ |
| A-95 | $CH(CH_3)CH(C_2H_5)_2$ |
| A-96 | $C(CH_3)_2CH(CH_3)C_2H_5$ |
| A-97 | $CH(C_2H_5)CH(CH_3)C_2H_5$ |
| A-98 | $C(CH_3)(C_2H_5)-n-C_3H_7$ |
| A-99 | $CH(n-C_3H_7)_2$ |
| A-100 | $CH(n-C_3H_7)CH(CH_3)_2$ |
| A-101 | $C(CH_3)_2C(CH_3)_3$ |
| A-102 | $C(CH_3)(C_2H_5)-CH(CH_3)_2$ |
| A-103 | $C(C_2H_5)_3$ |
| A-104 | $(3-CH_3)-c-C_6H_{10}$ |
| A-105 | $(2-CH_3)-c-C_6H_{10}$ |
| A-106 | $n-C_8H_{17}$ |
| A-107 | $CH_2C(=NO-CH_3)CH_3$ |
| A-108 | $CH_2C(=NO-C_2H_5)CH_3$ |
| A-109 | $CH_2C(=NO-n-C_3H_7)CH_3$ |
| A-110 | $CH_2C(=NO-i-C_3H_7)CH_3$ |
| A-111 | $CH(CH_3)C(=NOCH_3)CH_3$ |
| A-112 | $CH(CH_3)C(=NOC_2H_5)CH_3$ |
| A-113 | $CH(CH_3)C(=NO-n-C_3H_7)CH_3$ |
| A-114 | $CH(CH_3)C(=NO-i-C_3H_7)CH_3$ |
| A-115 | $C(=NOCH_3)C(=NOCH_3)CH_3$ |
| A-116 | $C(=NOCH_3)C(=NOC_2H_5)CH_3$ |
| A-117 | $C(=NOCH_3)C(=NO-n-C_3H_7)CH_3$ |
| A-118 | $C(=NOCH_3)C(=NO-i-C_3H_7)CH_3$ |
| A-119 | $C(=NOC_2H_5)C(=NOCH_3)CH_3$ |
| A-120 | $C(=NOC_2H_5)C(=NOC_2H_5)CH_3$ |
| A-121 | $C(=NOC_2H_5)C(=NO-n-C_3H_7)CH_3$ |
| A-122 | $C(=NOC_2H_5)C(=NO-i-C_3H_7)CH_3$ |
| A-123 | $CH_2C(=NO-CH_3)C_2H_5$ |
| A-124 | $CH_2C(=NO-C_2H_5)C_2H_5$ |
| A-125 | $CH_2C(=NO-n-C_3H_7)C_2H_5$ |
| A-126 | $CH_2C(=NO-i-C_3H_7)C_2H_5$ |
| A-127 | $CH(CH_3)C(=NOCH_3)C_2H_5$ |
| A-128 | $CH(CH_3)C(=NOC_2H_5)C_2H_5$ |
| A-129 | $CH(CH_3)C(=NO-n-C_3H_7)C_2H_5$ |
| A-130 | $CH(CH_3)C(=NO-n-C_3H_7)C_2H_5$ |
| A-131 | $C(=NOCH_3)C(=NOCH_3)C_2H_5$ |
| A-132 | $C(=NOCH_3)C(=NOC_2H_5)C_2H_5$ |
| A-133 | $C(=NOCH_3)C(=NO-n-C_3H_7)C_2H_5$ |
| A-134 | $C(=NOCH_3)C(NO-i-C_3H_7)C_2H_5$ |
| A-135 | $C(=NOC_2H_5)C(=NOCH_3)C_2H_5$ |
| A-136 | $C(=NOC_2H_5)C(=NOC_2H_5)C_2H_5$ |
| A-137 | $C(=NOC_2H_5)C(=NO-n-C_3H_7)C_2H_5$ |
| A-138 | $C(=NOC_2H_5)C(=NO-i-C_3H_7)C_2H_5$ |
| A-139 | $CH=CH-CH_2CH_3$ |
| A-140 | $CH_2-CH=CH-CH_3$ |
| A-141 | $CH_2-CH_2-CH=CH_2$ |
| A-142 | $C(CH_3)_2CH_2CH_3$ |
| A-143 | $CH=C(CH_3)_2$ |
| A-144 | $C(=CH_2)-CH_2CH_3$ |
| A-145 | $C(CH_3)=CH-CH_3$ |
| A-146 | $CH(CH_3)CH=CH_2$ |
| A-147 | $CH=CH-n-C_3H_7$ |
| A-148 | $CH_2-CH=CH-C_2H_5$ |
| A-149 | $(CH_2)_2-CH=CH-CH_3$ |
| A-150 | $(CH_2)_3-CH=CH_2$ |
| A-151 | $CH=CH-CH(CH_3)_2$ |
| A-152 | $CH_2-CH=C(CH_3)_2$ |
| A-153 | $(CH_2)_2-C(CH_3)=CH_2$ |
| A-154 | $CH=C(CH_3)-C_2H_5$ |
| A-155 | $CH_2-C(=CH_2)-C_2H_5$ |
| A-156 | $CH_2-C(CH_3)=CH-CH_3$ |
| A-157 | $CH_2-CH(CH_3)-CH=CH_2$ |
| A-158 | $C(=CH_2)-CH_2-CH_2-CH_3$ |
| A-159 | $C(CH_3)=CH-CH_2-CH_3$ |
| A-160 | $CH(CH_3)-CH=CH-CH_3$ |
| A-161 | $CH(CH_3)-CH_2-CH=CH_2$ |
| A-162 | $C(=CH_2)CH(CH_3)_2$ |
| A-163 | $C(CH_3)=C(CH_3)_2$ |
| A-164 | $CH(CH_3)-C(=CH_2)-CH_3$ |
| A-165 | $C(CH_3)_2-CH=CH_2$ |
| A-166 | $C(C_2H_5)=CH-CH_3$ |
| A-167 | $C(C_2H_5)-CH=CH_2$ |
| A-168 | $CH=CH-CH_2-CH_2-CH_2-CH_3$ |
| A-169 | $CH_2-CH=CH-CH_2-CH_2-CH_3$ |
| A-170 | $CH_2-CH_2-CH=CH-CH_2-CH_3$ |
| A-171 | $CH_2-CH_2-CH_2-CH=CH-CH_3$ |
| A-172 | $CH_2-CH_2-CH_2-CH_2-CH=CH_2$ |
| A-173 | $CH=CH-CH_2-CH(CH_3)CH_3$ |
| A-174 | $CH_2-CH=CH-CH(CH_3)CH_3$ |
| A-175 | $CH_2-CH_2-CH=C(CH_3)CH_3$ |
| A-176 | $CH_2-CH_2-CH_2-C(CH_3)=CH_2$ |
| A-177 | $CH=CH-CH(CH_3)-CH_2-CH_3$ |
| A-178 | $CH_2-CH=C(CH_3)-CH_2-CH_3$ |
| A-179 | $CH_2-C(=CH_2)-CH_2-CH_3$ |
| A-180 | $CH_2-CH_2-C(CH_3)=CH-CH_3$ |
| A-181 | $CH_2-CH_2-CH(CH_3)-CH=CH_2$ |
| A-182 | $CH=C(CH_3)-CH_2-CH_2-CH_3$ |
| A-183 | $CH_2-C(=CH_2)-CH_2-CH_2-CH_3$ |
| A-184 | $CH_2-C(CH_3)=CH-CH_2-CH_3$ |
| A-185 | $CH_2-CH(CH_3)-CH=CH-CH_3$ |
| A-186 | $CH_2-CH(CH_3)-CH_2-CH=CH_2$ |
| A-187 | $C(=CH_2)-CH_2-CH_2-CH_2-CH_3$ |
| A-188 | $C(CH_3)=CH-CH_2-CH_2-CH_3$ |
| A-189 | $CH(CH_3)-CH=CH-CH_2-CH_3$ |
| A-190 | $CH(CH_3)-CH_2-CH=CH-CH_3$ |
| A-191 | $CH(CH_3)-CH_2-CH_2-CH=CH_2$ |
| A-192 | $CH=CH-C(CH_3)_3$ |

TABLE A-continued

| No. | R¹ |
|---|---|
| A-193 | CH=C(CH₃)—CH(CH₃)—CH₃ |
| A-194 | CH₂—C(=CH₂)—CH(CH₃)—CH₃ |
| A-195 | CH₂—C(CH₃)=C(CH₃)—CH₃ |
| A-196 | CH₂—CH(CH₃)—C(=CH₂)—CH₃ |
| A-197 | C(=CH₂)—CH₂—CH(CH₃)—CH₃ |
| A-198 | C(CH₃)=CH—CH(CH₃)—CH₃ |
| A-199 | CH(CH₃)—CH=C(CH₃)—CH₃ |
| A-200 | CH(CH₃)—CH₂—C(=CH₂)—CH₃ |
| A-201 | CH=C(CH₂—CH₃)—CH₂—CH₃ |
| A-202 | CH₂—C(=CH—CH₃)—CH₂—CH₃ |
| A-203 | CH₂—CH(CH=CH₂)—CH₂—CH₃ |
| A-204 | C(=CH—CH₃)—CH₂—CH₂—CH₃ |
| A-205 | CH(CH=CH₂)—CH₂—CH₂—CH₃ |
| A-206 | C(CH₂—CH₃)=CH—CH₂—CH₃ |
| A-207 | CH(CH₂—CH₃)—CH=CH—CH₃ |
| A-208 | CH(CH₂—CH₃)—CH₂—CH=CH₂ |
| A-209 | CH₂—C(CH₃)₂—CH=CH₂ |
| A-210 | C(=CH₂)—CH(CH₃)—CH₂—CH₃ |
| A-211 | C(CH₃)=C(CH₃)—CH₂—CH₃ |
| A-212 | CH(CH₃)—C(=CH₂)—CH₂—CH₃ |
| A-213 | CH(CH₃)—C(CH₃)=CH—CH₃ |
| A-214 | CH(CH₃)—CH(CH₃)—CH=CH₂ |
| A-215 | C(CH₃)₂—CH=CH—CH₃ |
| A-216 | C(CH₃)₂—CH₂—CH=CH₂ |
| A-217 | C(=CH₂)—C(CH₃)₃ |
| A-218 | C(=CH—CH₃)—CH(CH₃)—CH₃ |
| A-219 | CH(CH=CH₂)—CH(CH₃)—CH₃ |
| A-220 | C(CH₂—CH₃)=C(CH₃)—CH₃ |
| A-221 | CH(CH₂—CH₃)—C(=CH₂)—CH₃ |
| A-222 | C(CH₃)₂—C(=CH₂)—CH₃ |
| A-223 | C(CH₃)(CH=CH₂)—CH₂—CH₃ |
| A-224 | C(CH₃)(CH₂CH₃)—CH₂—CH₂—CH₃ |
| A-225 | CH(CH₂CH₃)—CH(CH₃)—CH₂—CH₃ |
| A-226 | CH(CH₂CH₃)—CH₂—CH(CH₃)—CH₃ |
| A-227 | C(CH₃)₂—C(CH₃)₃ |
| A-228 | C(CH₂—CH₃)—C(CH₃)₃ |
| A-229 | C(CH₃)(CH₂—CH₃)—CH(CH₃)₂ |
| A-230 | CH(CH(CH₃)₂)—CH(CH₃)₂ |
| A-231 | CH=CH—CH₂—CH₂—CH₂—CH₂—CH₃ |
| A-232 | CH₂—CH=CH—CH₂—CH₂—CH₂—CH₃ |
| A-233 | CH₂—CH₂—CH=CH—CH₂—CH₂—CH₃ |
| A-234 | CH₂—CH₂—CH₂—CH=CH—CH₂—CH₃ |
| A-235 | CH₂—CH₂—CH₂—CH₂—CH=CH—CH₃ |
| A-236 | CH₂—CH₂—CH₂—CH₂—CH₂—CH=CH₂ |
| A-237 | CH=CH—CH₂—CH₂—CH(CH₃)—CH₃ |
| A-238 | CH₂—CH=CH—CH₂—CH(CH₃)—CH₃ |
| A-239 | CH₂—CH₂—CH=CH—CH(CH₃)—CH₃ |
| A-240 | CH₂—CH₂—CH₂—CH=C(CH₃)—CH₃ |
| A-241 | CH₂—CH₂—CH₂—CH₂—C(=CH₂)—CH₃ |
| A-242 | CH=CH—CH₂—CH(CH₃)—CH₂—CH₃ |
| A-243 | CH₂—CH=CH—CH(CH₃)—CH₂—CH₃ |
| A-244 | CH₂—CH₂—CH=C(CH₃)—CH₂—CH₃ |
| A-245 | CH₂—CH₂—CH₂—C(=CH₂)—CH₂—CH₃ |
| A-246 | CH₂—CH₂—CH₂—C(CH₃)=CH—CH₃ |
| A-247 | CH₂—CH₂—CH₂—CH(CH₃)—CH=CH₂ |
| A-248 | CH=CH—CH(CH₃)—CH₂—CH₂—CH₃ |
| A-249 | CH₂—CH=C(CH₃)—CH₂—CH₂—CH₃ |
| A-250 | CH₂—CH₂—C(=CH₂)—CH₂—CH₂—CH₃ |
| A-251 | CH₂—CH₂—C(CH₃)=CH—CH₂—CH₃ |
| A-252 | CH₂—CH₂—CH(CH₃)—CH=CH—CH₃ |
| A-253 | CH₂—CH₂—CH(CH₃)—CH₂—CH=CH₂ |
| A-254 | CH=C(CH₃)—CH₂—CH₂—CH₂—CH₃ |
| A-255 | CH₂—C(=CH₂)—CH₂—CH₂—CH₂—CH₃ |
| A-256 | CH₂—C(CH₃)=CH—CH₂—CH₂—CH₃ |
| A-257 | CH₂—CH(CH₃)—CH=CH—CH₂—CH₃ |
| A-258 | CH₂—CH(CH₃)—CH₂—CH=CH—CH₃ |
| A-259 | CH₂—CH(CH₃)—CH₂—CH₂—CH=CH₂ |
| A-260 | C(=CH₂)—CH₂—CH₂—CH₂—CH₂—CH₃ |
| A-261 | C(CH₃)=CH—CH₂—CH₂—CH₂—CH₃ |
| A-262 | CH(CH₃)—CH=CH—CH₂—CH₂—CH₃ |
| A-263 | CH(CH₃)—CH₂—CH=CH—CH₂—CH₃ |
| A-264 | CH(CH₃)—CH₂—CH₂—CH=CH—CH₃ |
| A-265 | CH(CH₃)—CH₂—CH₂—CH₂—CH=CH₂ |
| A-266 | CH=CH—CH₂—C(CH₃)₃ |
| A-267 | CH₂—CH=CH—C(CH₃)₃ |
| A-268 | CH=CH—CH(CH₃)—CH(CH₃)₂ |
| A-269 | CH₂—CH=C(CH₃)—CH(CH₃)₂ |
| A-270 | CH₂—CH₂—C(=CH₂)—CH(CH₃)₂ |
| A-271 | CH₂—CH₂—C(CH₃)=C(CH₃)₂ |
| A-272 | CH₂—CH₂—CH(CH₃)—C(=CH₂)—CH₃ |
| A-273 | CH=C(CH₃)—CH₂—CH(CH₃)₂ |
| A-274 | CH₂—C(=CH₂)—CH₂—CH(CH₃)₂ |
| A-275 | CH₂—C(CH₃)₂—CH₂—CH(CH₃)₂ |
| A-276 | CH₂—CH(CH₃)—CH=C(CH₃)₂ |
| A-277 | CH₂—CH(CH₃)—CH₂—C(=CH₂)—CH₃ |
| A-278 | C(=CH₂)—CH₂—CH₂—CH(CH₃)₂ |
| A-279 | C(CH₃)=CH—CH₂—CH(CH₃)₂ |
| A-280 | CH(CH₃)—CH=CH—CH(CH₃)₂ |
| A-281 | CH(CH₃)—CH₂—CH=C(CH₃)₂ |
| A-282 | CH(CH₃)—CH₂—CH₂—C(=CH₂)—CH₃ |
| A-283 | CH=CH—C(CH₃)₂—CH₂—CH₃ |
| A-284 | CH₂—CH₂—C(CH₃)₂—CH=CH₂ |
| A-285 | CH=C(CH₃)—CH(CH₃)—CH₂—CH₃ |
| A-286 | CH₂—C(=CH₂)—CH(CH₃)—CH₂—CH₃ |
| A-287 | CH₂—C(CH₃)=C(CH₃)—CH₂—CH₃ |
| A-288 | CH₂—CH(CH₃)—C(=CH₂)—CH₂—CH₃ |
| A-289 | CH₂—CH(CH₃)—C(CH₃)=CH—CH₃ |
| A-290 | CH₂—CH(CH₃)—CH(CH₃)—CH=CH₂ |
| A-291 | C(=CH₂)—CH₂—CH(CH₃)—CH₂—CH₃ |
| A-292 | C(CH₃)=CH—CH(CH₃)—CH₂—CH₃ |
| A-293 | CH(CH₃)—CH=C(CH₃)—CH₂—CH₃ |
| A-294 | CH(CH₃)—CH₂—C(=CH₂)—CH₂—CH₃ |
| A-295 | CH(CH₃)—CH₂—C(CH₃)=CH—CH₃ |
| A-296 | CH(CH₃)—CH₂—CH(CH₃)—CH=CH₂ |
| A-297 | CH₂—C(CH₃)₂—CH=CH—CH₃ |
| A-298 | CH₂—C(CH₃)₂—CH₂—CH=CH₂ |
| A-299 | C(=CH₂)—CH(CH₃)—CH₂—CH₂—CH₃ |
| A-300 | C(CH₃)=CH—CH₂—CH₂—CH₂—CH₃ |
| A-301 | CH(CH₃)—C(=CH₂)—CH₂—CH₂—CH₃ |
| A-302 | CH(CH₃)—C(CH₃)=CH—CH₂—CH₃ |
| A-303 | CH(CH₃)—CH(CH₃)—CH=CH—CH₃ |
| A-304 | CH(CH₃)—CH(CH₃)—CH₂—CH=CH₂ |
| A-305 | C(CH₃)₂—CH=CH—CH₂—CH₃ |
| A-306 | C(CH₃)₂—CH₂—CH=CH—CH₃ |
| A-307 | C(CH₃)₂—CH₂—CH₂—CH=CH₂ |
| A-308 | CH=CH—CH(CH₂—CH₃)—CH₂—CH₃ |
| A-309 | CH₂—CH=C(CH₂—CH₃)—CH₂—CH₃ |
| A-310 | CH₂—CH₂—C(=CH—CH₃)—CH₂—CH₃ |
| A-311 | CH₂—CH₂—CH(CH=CH₂)—CH₂—CH₃ |
| A-312 | CH=C(CH₂—CH₃)—CH₂—CH₂—CH₃ |
| A-313 | CH₂—C(=CH—CH₃)—CH₂—CH₂—CH₃ |
| A-314 | CH₂—CH(CH=CH₂)—CH₂—CH₂—CH₃ |
| A-315 | CH₂—C(CH₂—CH₃)=CH—CH₂—CH₃ |
| A-316 | CH₂—CH(CH₂—CH₃)—CH=CH—CH₃ |
| A-317 | CH₂—CH(CH₂—CH₃)—CH₂—CH=CH₂ |
| A-318 | C(=CH—CH₃)—CH₂—CH₂—CH₂—CH₃ |
| A-319 | CH(CH=CH₂)—CH₂—CH₂—CH₂—CH₃ |
| A-320 | C(CH₂—CH₃)=CH—CH₂—CH₂—CH₃ |
| A-321 | CH(CH₂—CH₃)—CH=CH—CH₂—CH₃ |
| A-322 | CH(CH₂—CH₃)—CH₂—CH=CH—CH₃ |
| A-323 | CH(CH₂—CH₃)—CH₂—CH₂—CH=CH₂ |
| A-324 | C(=CH—CH₂—CH₃)—CH₂—CH₂—CH₃ |
| A-325 | C(CH=CH—CH₃)—CH₂—CH₂—CH₃ |
| A-326 | C(CH₂—CH=CH₂)—CH₂—CH₂—CH₃ |
| A-327 | CH=C(CH₃)—C(CH₃)₃ |
| A-328 | CH₂—C(=CH₂)—C(CH₃)₃ |
| A-329 | CH₂—C(CH₃)₂—CH(=CH₂)—CH₃ |
| A-330 | C(=CH₂)—CH(CH₃)—CH(CH₃)—CH₃ |
| A-331 | C(CH₃)=C(CH₃)—CH(CH₃)—CH₃ |
| A-332 | CH(CH₃)—C(=CH₂)—CH(CH₃)—CH₃ |
| A-333 | CH(CH₃)—C(CH₃)=C(CH₃)—CH₃ |
| A-334 | CH(CH₃)—CH(CH₃)—C(=CH₂)—CH₃ |
| A-335 | C(CH₃)₂—CH=C(CH₃)—CH₃ |
| A-336 | C(CH₃)₂—CH₂—C(=CH₂)—CH₃ |
| A-337 | C(CH₃)₂—C(=CH₂)—CH₂—CH₃ |
| A-338 | C(CH₃)₂—C(CH₃)=CH—CH₃ |
| A-339 | C(CH₃)₂—CH(CH₃)CH=CH₂ |
| A-340 | CH(CH₂—CH₃)—CH₂—CH(CH₃)—CH₃ |
| A-341 | CH(CH₂—CH₃)—CH(CH₃)—CH₂—CH₃ |
| A-342 | C(CH₃)(CH₂—CH₃)—CH₂—CH₂—CH₃ |
| A-343 | CH(i-C₃H₇)—CH₂—CH₂—CH₃ |
| A-344 | CH=C(CH₂—CH₃)—CH(CH₃)—CH₃ |
| A-345 | CH₂—C(=CH—CH₃)—CH(CH₃)—CH₃ |
| A-346 | CH₂—CH(CH=CH₂)—CH(CH₃)—CH₃ |

TABLE A-continued

| No. | R$^1$ |
|---|---|
| A-347 | CH$_2$—C(CH$_2$—CH$_3$)=C(CH$_3$)—CH$_3$ |
| A-348 | CH$_2$—CH(CH$_2$—CH$_3$)—C(=CH$_2$)—CH$_3$ |
| A-349 | CH$_2$—C(CH$_3$)(CH=CH$_2$)—CH$_2$—CH$_3$ |
| A-350 | C(=CH$_2$)—CH(CH$_2$—CH$_3$)—CH$_2$—CH$_3$ |
| A-351 | C(CH$_3$)=C(CH$_2$—CH$_3$)—CH$_2$—CH$_3$ |
| A-352 | CH(CH$_3$)—C(=CH—CH$_3$)—CH$_2$—CH$_3$ |
| A-353 | CH(CH$_3$)—CH(CH=CH$_2$)—CH$_2$—CH$_3$ |
| A-354 | CH=C(CH$_2$—CH$_3$)—CH(CH$_3$)—CH$_3$ |
| A-355 | CH$_2$—C(=CH—CH$_3$)—CH(CH$_3$)—CH$_3$ |
| A-356 | CH$_2$—CH(CH=CH$_2$)—CH(CH$_3$)—CH$_3$ |
| A-357 | CH$_2$—C(CH$_2$—CH$_3$)=C(CH$_3$)—CH$_3$ |
| A-358 | CH$_2$—CH(CH$_2$—CH$_3$)—C(=CH$_2$)—CH$_3$ |
| A-359 | C(=CH—CH$_3$)—CH$_2$—CH(CH$_3$)—CH$_3$ |
| A-360 | CH(CH=CH$_2$)—CH$_2$—CH(CH$_3$)—CH$_3$ |
| A-361 | C(CH$_2$—CH$_3$)=CH—CH(CH$_3$)—CH$_3$ |
| A-362 | CH(CH$_2$—CH$_3$)CH=C(CH$_3$)—CH$_3$ |
| A-363 | CH(CH$_2$—CH$_3$)CH$_2$—C(=CH$_2$)—CH$_3$ |
| A-364 | C(=CH—CH$_3$)CH(CH$_3$)—CH$_2$—CH$_3$ |
| A-365 | CH(CH=CH$_2$)CH(CH$_3$)—CH$_2$—CH$_3$ |
| A-366 | C(CH$_2$—CH$_3$)=C(CH$_3$)—CH$_2$—CH$_3$ |
| A-367 | CH(CH$_2$—CH$_3$)—C(=CH$_2$)—CH$_2$—CH$_3$ |
| A-368 | CH(CH$_2$—CH$_3$)—C(CH$_3$)=CH—CH$_3$ |
| A-369 | CH(CH$_2$—CH$_3$)—CH(CH$_3$)—CH=CH$_2$ |
| A-370 | C(CH$_3$)(CH=CH$_2$)—CH$_2$—CH$_2$—CH$_3$ |
| A-371 | C(CH$_3$)(CH$_2$—CH$_3$)—CH=CH—CH$_3$ |
| A-372 | C(CH$_3$)(CH$_2$—CH$_3$)—CH$_2$—CH=CH$_2$ |
| A-373 | C[=C(CH$_3$)—CH$_3$]—CH$_2$—CH$_2$—CH$_3$ |
| A-374 | CH[C(=CH$_2$)—CH$_3$]—CH$_2$—CH$_2$—CH$_3$ |
| A-375 | C(i-C$_3$H$_7$)=CH—CH$_2$—CH$_3$ |
| A-376 | CH(i-C$_3$H$_7$)—CH=CH—CH$_3$ |
| A-377 | CH(i-C$_3$H$_7$)—CH$_2$—CH=CH$_2$ |
| A-378 | C(=CH—CH$_3$)—C(CH$_3$)$_3$ |
| A-379 | CH(CH=CH$_2$)—C(CH$_3$)$_3$ |
| A-380 | C(CH$_3$)(CH=CH$_2$)CH(CH$_3$)—CH$_3$ |
| A-381 | C(CH$_3$)(CH$_2$—CH$_3$)C(=CH$_2$)—CH$_3$ |
| A-382 | 2-CH$_3$-Cyclohex-1-enyl |
| A-383 | [2-(=CH$_2$)]-c-C$_6$H$_9$ |
| A-384 | 2-CH$_3$-Cyclohex-2-enyl |
| A-385 | 2-CH$_3$-Cyclohex-3-enyl |
| A-386 | 2-CH$_3$-Cyclohex-4-enyl |
| A-387 | 2-CH$_3$-Cyclohex-5-enyl |
| A-388 | 2-CH$_3$-Cyclohex-6-enyl |
| A-389 | 3-CH$_3$-Cyclohex-1-enyl |
| A-390 | 3-CH$_3$-Cyclohex-2-enyl |
| A-391 | [3-(=CH$_2$)]-c-C$_6$H$_9$ |
| A-392 | 3-CH$_3$-Cyclohex-3-enyl |
| A-393 | 3-CH$_3$-Cyclohex-4-enyl |
| A-394 | 3-CH$_3$-Cyclohex-5-enyl |
| A-395 | 3-CH$_3$-Cyclohex-6-enyl |
| A-396 | 4-CH$_3$-Cyclohex-1-enyl |
| A-397 | 4-CH$_3$-Cyclohex-2-enyl |
| A-398 | 4-CH$_3$-Cyclohex-3-enyl |
| A-399 | [4-(=CH$_2$)]-c-C$_6$H$_9$ |

The compounds I are suitable as fungicides. They have excellent activity against a broad spectrum of phytopathogenic fungi, in particular from the class of the *Ascomycetes, Deuteromycetes, Phycomycetes* and *Basidiomycetes*. Some of them act systemically and can be employed in crop protection as foliar- and soil-acting fungicides.

They are especially important for controlling a large number of fungi in a variety of crop plants such as wheat, rye, barley, oats, rice, maize, grass, bananas, cotton, soybean, coffee, sugar cane, grapevines, fruit species, ornamentals and vegetable species such as cucumbers, beans, tomatoes, potatoes and cucurbits, and also in the seeds of these plants.

Specifically, they are suitable for controlling the following plant diseases:

*Alternaria* species in vegetables and fruit,
*Botrytis cinerea* (gray mold) in strawberries, vegetables, ornamentals and grapevines,
*Cercospora arachidicola* in groundnuts,
*Erysiphe cichoracearum* and *Sphaerotheca fuliginea* in cucurbits,
*Erysiphe graminis* (powdery mildew) in cereals,
*Fusarium* and *Verticillium* species in a variety of plants,
*Helminthosporium* species in cereals,
*Mycosphaerella* species in bananas and groundnuts,
*Phytophthora infestans* in potatoes and tomatoes,
*Plasmopara viticola* in grapevines,
*Podosphaera leucotricha* in apples,
*Pseudocercosporella herpotrichoides* in wheat and barley,
*Pseudoperonospora* species in hops and cucumbers,
*Puccinia* species in cereals,
*Pyricularia oryzae* in rice,
*Rhizoctonia* species in cotton, rice and lawns,
*Septoria nodorum* in wheat,
*Uncinula necator* in grapevines,
*Ustilago* species in cereals and sugar cane, and
*Venturia* species (scab) in apples and pears.

The compounds I are also suitable for controlling harmful fungi such as *Paecilomyces variotii* in the protection of materials (for example wood, paper, paint dispersions, fibers or tissues) and in the protection of stored products.

The compounds I are employed by treating the fungi or the plants, seeds, materials or the soil to be protected against fungal attack with a fungicidally effective amount of the active compounds. The application can be carried out before or after the infection of the materials, plants or seeds by the fungi.

The fungicidal compositions generally comprise from 0.1 to 95, preferably from 0.5 to 90, % by weight of active compound.

For use in crop protection, the application rates are, depending on the kind of effect desired, from 0.01 to 2.0 kg of active compound per ha.

The treatment of seeds generally requires active compound rates of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds I can be converted into the customary formulations, e.g. solutions, emulsions, suspensions, dusts, powders, pastes and granules. The use form depends on the specific intended use; in any case, it should ensure fine and uniform distribution of the compound according to the invention.

The formulations are prepared in a known manner, e.g. by extending the active compound with solvents and/or carriers, if desired using emulsifiers and dispersants, it being possible to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates), and dispersants such as lignosulfite waste liquors and methylcellulose.

Suitable surfactants are the alkali metal, alkaline earth metal and ammonium salts of lignosulfonic acid, naphthalenesulfonic acid, phenolsulfonic acid, and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for preparing directly sprayable solutions, emulsions, pastes or oil dispersions are petroleum fractions having medium to high boiling points, such as kerosene or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or joint grinding of the active substances with a solid carrier.

Granules, for example coated granules, impregnated granules and homogenous granules, can be prepared by binding the active compounds to solid carriers. Solid carriers are, for example, mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of plant origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of Formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 6 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol. 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-α-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100 000 parts by weight of water and finely dispersed therein, affording an aqueous dispersion comprising 0.02% by weight of active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20 000 parts by weight of water, affording a spray liquor comprising 0.1% by weight of active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should ensure very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active compound, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with a high degree of success in the ultra-low-volume method (ULV), it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, mixing of the compounds I, or of the compositions comprising them, in the use form as fungicides with other fungicides results in a broader fungicidal spectrum of activity.

The following list of fungicides, in combination with which the compounds according to the invention can be used, is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2-cloro-N-(4'-chlorobiphenyl-2-yl)nicotineamide 2,4-dichloro-6-(o-chloroanilino)-s-triazine, O,O-diethyl phthalimidophosphonothioate. 5-amino-1-[bis(dimethylamino)phosphinyl]-3-phenyl-1,2,4-triazole, 2,3-dicyano-1,4-dithioanthraquinone. 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenyl-sulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, o-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis-1-(2,2,2-trichloroethyl)formamide, 1-(3,4-dichloroanilino)-1-formylamino-2,2,2-trichloroethane 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylure a, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)oxiran-2-ylmethyl)-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene;

strobilurins, such as methyl-E-methoximino-[α-(o-tolyloxy)-o-tolyl]acetate, methyl E-2-{2-[6-(2-cyanophenoxy)-pyrimidin-4-yloxy]-phenyl}-3-methoxyacrylate, methyl-E-methoximino-[α-(2-phenoxyphenyl)]acetamide, methyl-E-methoximino-[α-(2,5-dimethylphenoxy)-o-tolyl]acetamide, methyl E-2-{2-[2-trifluoromethylpyrid-6-yl]oxymethyl)phenyl}-3-methoxyacrylate, methyl (E,E)-methoximino-{2-[1-(3-trifluoromethylphenyl)ethylidene-aminooxymethyl]phenyl}acetate, methyl N-(2-{[1-(4-chlorophenyl)-1H-pyrazol-3-yl]oxymethyl}phenyl)-N-methoxycarbamate;

anilinopyrimidines, such as N-(4,6-dimethylpyrimidin-2-yl)aniline, N-(4-methyl-6-(1-propynyl)pyrimidin-2-yl]aniline, N-[4-methyl-6-cyclopropylpyrimidin-2-yl]aniline;

phenylpyrroles, such as 4-(2,2-difluoro-1,3-benzodioxol-4-yl)pyrrole-3-carbonitrile;

cinnamamides, such as 3-(4-chlorophenyl)-3-(3,4-dimethoxyphenyl)acryloylmorpholide, 3-(4-fluorophenyl)-3-(3,4-dimethoxy-phenyl)acryloylmorpholide;

and a variety of fungicides, such as dodecylguanidine acetate, 1-(3-bromo-6-methoxy-2-methylphenyl)-1-(2,3,4-trimethoxy-6-methylphenyl)methanone, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxy-methyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-(2-(2,4-dichlorophenyl)pentyl)-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoro-methyl-3-chloro-2-aminopyridine, 1-((bis-(4-fluorophenyl)methylsilyl)methyl)-1H-1,2,4-triazole, dimethyl-5-chloro-2-cyano-4-p-tolylimidazole-1-sulfonamide, 3,5-dichloro-N-(3-chloro-1-ethyl-1-methyl-2-oxopropyl)-4-methylbenzamide.

SYNTHESIS EXAMPLES

The procedures given in the synthesis examples below were used to obtain further compounds I by appropriate modification of the starting materials. The compounds obtained in this manner are listed in the tables that follow, together with physical data.

Example 1

Preparation of 5,7-dimethyl-6-phenyl-1,2,4-triazolo[1,5a]pyrimidine [I-1]

A mixture of 0.84 g (10 mmol) of 3-aminotriazole and 1.8 g (28 mmol) of 3-phenylpentane-2,4-dione in 5 g of tributylamine as heated at 140° C.-180° C. for 8 hours. After cooling to 20-25° C., the precipitate was filtered off and washed with diisopropyl ether. This gave 0.3 g of the title compound as colorless crystals. The filtrate was extracted with dil. hydrochloric acid and the organic phase was discarded. Following neutralization, the aqueous phase was extracted with ethyl acetate and concentrated. The residue gave, after silica gel chromatography (cyclohexane/ethyl acetate mixtures), an additional 0.5 g (total 36%) of the title compound as a yellowish crystalline material.

$^1$H-NMR (CDCl$_3$, δ in ppm): 8.5 (s, 1H); 7.5 (m, 3H); 7.2 (m, 2H) 2.6 (s, 3H); 2.45 (s, 3H).

Example 2

Preparation of 7-cyclohexyl-5-methyl-6-(2-Cl-,6-F-phenyl)-1,2,4-triazolo[1,5a]pyrimidine [I-4]

a) 7-cyclohexyl-5-(diethylmalon-2-yl)-6-(2-Cl-,6-F-phenyl)-1,2,4-triazolo[1,5a]pyrimidine A mixture of 30 g (0.18 mol) of diethyl malonate in 30 ml of acetonitrile was treated with 0.3 g (12 mmol) of sodium hydride. 2.8 g (7.6 mmol) of 5-chloro-7-cyclohexyl-6-(2-Cl-,6-F-phenyl)-1,2,4-triazolo[1,5a]pyrimidine (WO-A 99/41255) were then added, and the reaction mixture was stirred at about 70° C. for approximately 5 hours. The sodium salt of the product precipitated as a yellow solid which was filtered off and washed with acetonitrile. The residue was mixed with a little kieselguhr and stirred with a mixture of dil. hydrochloric acid and ethyl acetate. The acetonitrile washing phase was likewise stirred with dil. hydrochloric acid/ethyl acetate. The combined ethyl acetate phases were dried and concentrated. The residue crystallized and was digested with diisopropyl ether. This gave 1.4 g (38%) of the title compound as a colorless solid.

$^1$H-NMR (CDCl$_3$, δ in ppm): 8.55 (s, 1H); 7.5 (m, 2H); 7.2 (t, 1H) 4.6 (s, 1H); 4.0-4.4 (m, 4H); 2.3-2.9 (m, 3H); 1.6-1.9 (m, 5H); 1.05-1.4 (m, 9H).

b) 7-cyclohexyl-5-methyl-6-(2-chloro-,6-fluorophenyl)-1,2,4-triazolo[1,5a]pyrimidine A mixture of 1.1 g (2.2 mmol) of 7-cyclohexyl-5-(diethylmalon-2-yl)-6-(2-Cl-,6-F-phenyl)-1,2,4-triazolo[1,5a]pyrimidine (Example 2a) in 10 ml of conc. hydrochloric acid was stirred at 80-90° C. for 2 hours. After cooling to 20-25° C., the mixture was diluted with water and the aqueous phase was extracted with CH$_2$Cl$_2$. The combined organic phases were washed with sodium carbonate solution, dried and concentrated. The residue crystallized and was digested with diisopropyl ether. This gave 0.5 g (66%) of the title compound as a colorless solid of m.p. 182-184° C.

$^1$H-NMR (CDCl$_3$, δ in ppm): 8.5 (s, 1H); 7.5 (m, 2H); 7.2 (t, 1H); 2.2-2.9 (m, 3H); 2.6 (s, 3H); 1.6-1.9 (m, 5), 1.15-1.4 (m, 3H).

Example 3

Preparation of 7-isobutyl-5-ethyl-6-(2-Cl-,6-F-phenyl)-1,2,4-triazolo-[1,5a]pyrimidine [I-14]

A stream of argon was passed through a mixture of 1.7 g (5 mmol) of 5-Cl-7-isobutyl-6-(2-Cl-,6-F-phenyl)-1,2,4-triazolo[1,5a]pyrimidine (WO-A 99/41255) in 40 ml of tetrahydrofuran for about 15 min. 0.15 g (0.25 mmol) of (1,3-bis(diphenylphosphino)propane)nickel(II) chloride and 0.75 g (6 mmol) of diethylzinc were then added, and the mixture was stirred at 20-25° C. for approximately 3 hours. The reaction mixture was diluted with water and extracted with CH$_2$Cl$_2$. The combined organic phases were dried and concentrated. The residue gave, after silica gel chromatography (RP 18) with cyclohexane/ethyl acetate mixtures, 0.2 g (12%) of the title compound as a colorless solid of m.p. 106-108° C.

$^1$H-NMR (CDCl$_3$, δ in ppm): 8.5 (s, 1H); 7.5 (m, 1H); 7.45 (d, 1H); 7.2 (t, 1H); 3.05 (dd, 1H); 2.7 (m, 3H); 2.3 (m, 1H); 1.25 (t, 3H); 0.9 (d, 3H); 0.8 (d, 3H).

TABLE I

Compounds of the formula I

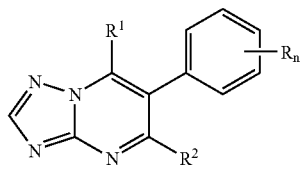

I

| No. | R$^1$ | R$^2$ | R$_n$ | Physical data (m.p.[° C.], IR[cm$^{-1}$], $^1$H-NMR[ppm]) |
|---|---|---|---|---|
| I-1 | CH$_3$ | CH$_3$ | — | 8.5(s, 1H); 7.5(m, 3H); 7.2(m, 2H); 2.6(s, 3H); 2.5(s, 3H) |
| I-2 | CH$_3$ | CH$_3$ | 2-Cl, 6-F | 117–121 |
| I-3 | (4-CH$_3$)-c-C$_6$H$_{10}$ | CH$_3$ | 2-Cl, 6-F | 190–192 |
| I-4 | c-C$_6$H$_{11}$ | CH$_3$ | 2-Cl, 6-F | 182–184 |
| I-5 | c-C$_5$H$_9$ | CH$_3$ | 2-Cl, 6-F | 179–181 |

TABLE I-continued

Compounds of the formula I

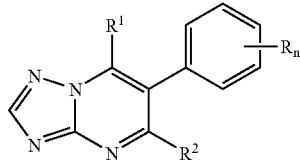

| No. | $R^1$ | $R^2$ | $R_n$ | Physical data (m.p.[° C.], IR[cm$^{-1}$], $^1$H-NMR[ppm]) |
|---|---|---|---|---|
| I-6 | $CH_2CH(CH_3)_2$ | $CH_3$ | 2-Cl, 6-F | 96–98 |
| I-7 | $c-C_6H_{11}$ | $CH_3$ | 2,4,6-$F_3$ | 159–161 |
| I-8 | $(CH_2)_3Cl$ | $CH_3$ | 2-Cl, 6-F | 96–98 |
| I-9 | $(1-CH_3)-c-C_3H_4$ | $CH_3$ | 2-Cl, 6-F | 176–178 |
| I-10 | $c-C_3H_5$ | $CH_3$ | 2-Cl, 6-F | 8.4(s, 1H); 7.5(m, 2H); 7,3(t, 1H); 2.4(s, 3H); 2.8(m, 3H), 1.1(m, 2H) |
| I-11 | $(CH_2)_2CH(CH_3)_2$ | $CH_3$ | 2-Cl, 6-F | 154–155 |
| I-12 | $C_6H_5$ | $CH_3$ | 2-Cl, 6-F | 215–217 |
| I-13 | $CH(CH_3)_2$ | $CH_3$ | 2-Cl, 6-F | 166–168 |
| I-14 | $CH_2CH(CH_3)CH_2CH_3$ | $CH_2CH_3$ | 2-Cl, 6-F | 106–108 |
| I-15 | (S) $CH_2CH(CH_3)CH_2CH_3$ | $CH_3$ | 2-Cl, 6-F | 99–101 |
| I-16 | $CH_2-C(=NO-CH_2-C_6H_5)-CH_3$ | $CH_3$ | 2,6-$F_2$, 4-$OCH_3$ | 1640, 1616, 1597, 1578, 1518, 101, 1440, 1275, 1200, 1191, 1151, 1137, 1122, 1042, 999 |
| I-17 | $CH_2-C(=NO-CH_3)-CH_3$ | $CH_3$ | 2,4,6-$F_3$ | 1639, 1618, 1597, 1518, 1498, 1439, 1397, 1276, 1238, 1190, 1123, 1055, 1041, 999, 848 |
| I-18 | $CH_2-C=NO-C_2H_5)-CH_3$ | $CH_3$ | 2,4,6-$F_3$ | 1638, 1617, 1597, 1518, 1498, 1439, 1397, 1276, 1238, 1191, 1123, 1052, 1041, 999 |
| I-19 | $CH_2-C(=NO-i-C_3H_7)-CH_3$ | $CH_3$ | 2,4,6-$F_3$ | 8.5 (2s); 4.1, 3.9 (2s); 2.5 (s); 1.8, 1.6 (2s) |
| I-20 | $CH_2-C(=NO-CH_3)-C_2H_5$ | $CH_3$ | 2,4,6-$F_3$ | 8.5 (s); 4.1, 3.95 (2s); 2.5 (2s); 1.0, 0.85 (2t) |
| I-21 | $CH_3$ | $CH_3$ | 2,4,6-$F_3$ | 148 |
| I-22 | $CH(CH_3)C_2H_5$ | $CH_3$ | 2,4,6-$F_3$ | 142 |
| I-23 | $CH_2-CH(CH_3)_2$ | $CH_3$ | 2,4,6-$F_3$ | 119 |
| I-24 | $CH_3$ | $CH_3$ | 2,6-$F_2$, 4-$O(CH_2)_2CH_3$ | 59 |
| I-25 | $n-C_4H_9$ | $CH_3$ | 2,4,6-$F_3$ | 2961, 1638, 1614, 1596, 120, 1498, 1438, 1397, 1274, 1238, 1122, 1039, 999, 843, 531 |
| I-26 | (S) $CH_2CH(CH_3)C_2H_5$ | $CH_3$ | 2,4,6-$F_3$ | 2964, 1638, 1610, 1596, 1516, 1498, 1438, 1277, 1238, 1192, 1122, 1039, 999, 843, 531 |
| I-27 | $c-C_3H_5$ | $CH_2CO-OC_2H_5$ | 2-Cl, 6-F | 1738, 1601, 1568, 1511, 1467, 1447, 1317, 1284, 1248, 1189, 1157, 1034, 981, 895, 789 |
| I-28 | $c-C_5H_9$ | $CH_3$ | 2,6-$F_2$, 4-CO—$OCH_3$ | 129 |
| I-29 | $(CH_2)_2-CH(CH_3)_2$ | $CH_3$ | 2,4,6-$F_3$ | 8.5 (s); 6.9 (m); 2.95 (m); 2,5 (s) |
| I-30 | $n-C_4H_9$ | $CH_3$ | 2,6-$F_2$ | 127 |
| I-31 | $CH_2CH(CH_3)_2$ | $CH_3$ | 2,6-$F_2$ | 107 |
| I-32 | $n-C_5H_{11}$ | $CH_3$ | 2,6-$F_2$ | 98 |
| I-33 | $CH(CH_3)(CH_2)_2CH_3$ | $CH_3$ | 2,6-$F_2$ | 138 |
| I-34 | $CH(C_2H_5)_2$ | $CH_3$ | 2,6-$F_2$ | 160 |
| I-35 | $c-C_5H_9$ | $CH_3$ | 2,6-$F_2$ | 192 |
| I-36 | $n-C_6H_{13}$ | $CH_3$ | 2,6-$F_2$ | 8.5 (s); 7.5 (m); 7.1 (m); 3.0 (m); 2.5 (s) |
| I-37 | $c-C_6H_{11}$ | $CH_3$ | 2,6-$F_2$ | 192 |
| I-38 | $CH(CH_3)C_2H_5$ | $CH_3$ | 2,6-$F_2$ | 163 |
| I-39 | $(CH_2)_2CH=CH_2$ | $CH_3$ | 2,4,6-$F_3$ | 120 |
| I-40 | $(CH_2)_2CH(Cl)CH_3$ | $CH_3$ | 2,4,6-$F_3$ | 75 |
| I-41 | $n-C_4H_9$ | $CH_3$ | 2,6-$F_2$ | 128 |
| I-42 | $n-C_6H_{13}$ | $CH_3$ | 2,6-$F_2$ | 148 |
| I-43 | $CH(CH_3)C_2H_5$ | $CH_3$ | 2,6-$F_2$ | 135 |
| I-44 | $n-C_5H_{11}$ | $CH_3$ | 2,6-$F_2$ | 102 |
| I-45 | $CH(C_2H_5)_2$ | $CH_3$ | 2,6-$F_2$ | 175 |
| I-46 | $CH(CH_3)(CH_2)_2CH_3$ | $CH_3$ | 2,6-$F_2$ | 132 |
| I-47 | $c-C_6H_{11}$ | $CH_3$ | 2-$CH_3$, 4-F | 8.5 (s); 2.3 (s); 2.1 (s) |
| I-48 | $c-C_5H_9$ | $CH_3$ | 2,6-$F_2$, 4-OH | 299 |
| I-49 | $CF_3$ | $CH_3$ | 2,4,6-$F_3$ | 131 |
| I-50 | $c-C_6H_{11}$ | $CH_3$ | 2,6-$F_2$, 4-$OCH_3$ | 185 |
| I-51 | $c-C_6H_{11}$ | $CH_3$ | 2,6-$F_2$, 4-$OCH_2CH_3$ | 8.5 (s); 6.65 (m); 4.1 (q); 2.5 (s) |

TABLE I-continued

Compounds of the formula I

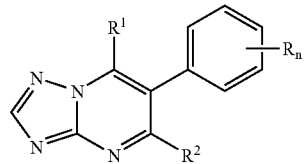

| No. | R$^1$ | R$^2$ | R$_n$ | Physical data (m.p.[° C.], IR[cm$^{-1}$], $^1$H-NMR[ppm]) |
|---|---|---|---|---|
| I-52 | c-C$_6$H$_{11}$ | CH$_3$ | 2,6-F$_2$, 4-O-n-C$_3$H$_7$ | 108 |
| I-53 | (4-CH$_3$)-c-C$_6$H$_{10}$ | CH$_3$ | 2,4,6-F$_3$ | 131 |
| I-54 | c-C$_6$H$_{11}$ | CH$_3$ | 2,6-F$_2$, 4-O-i-C$_3$H$_7$ | 212 |
| I-55 | c-C$_6$H$_{11}$ | CH$_3$ | 2,6-F$_2$, 4-OH | 290 |
| I-56 | c-C$_6$H$_{11}$ | CH$_3$ | 2,6-F$_2$, 4-CH=CH$_2$ | 207 |
| I-57 | c-C$_6$H$_{11}$ | CH$_3$ | 2,6-F$_2$, 4-C$_2$H$_5$ | 180 |
| I-58 | c-C$_6$H$_{11}$ | CH$_3$ | 2,6-F$_2$, 4-CN | 202 |
| I-59 | c-C$_6$H$_{11}$ | CH$_3$ | 2,6-F$_2$, 4-OCHF$_2$ | 165 |
| I-60 | c-C$_6$H$_{11}$ | CH$_3$ | 2,6-F$_2$, 4-OCH$_2$CO$_2$CH$_3$ | 8.5 (s); 6.65 (m); 4.7 (s); 3.9 (s); 2.45 (s) |
| I-61 | c-C$_6$H$_{11}$ | CH$_3$ | 2,6-F2, 4-OCH$_2$CH(OCH$_3$)$_2$ | 109 |
| I-62 | CH$_2$CH(CH$_3$)C$_2$H$_5$ | CH$_3$ | 2-F, 4-CH$_3$ | 8.45 (s); 7.1 (m); 3.05 (m); 2.8 (m); 2.45 (s); 2.4 (s) |
| I-63 | CH$_2$CH(CH$_3$)C$_2$H$_5$ | CH$_3$ | 4-F, 2-CH$_3$ | 120 |
| I-64 | (CH$_2$)$_2$—CH=CH$_2$ | CH$_3$ | 2,4,6-F$_3$ | 72 |
| I-65 | CH$_2$—CH=CH$_2$ | CH$_3$ | 2,4,6-F$_3$ | 1639, 1611, 1598, 1518, 1496, 1439, 1280, 11213, 1201, 1123, 1036, 1000, 917, 844, 661 |
| I-66 | CH$_2$—CH=CH$_2$ | CH$_3$ | 2,6-F$_2$, 4-OCH$_3$ | 82 |
| I-67 | n-C$_5$H$_{11}$ | CH$_3$ | 2,4,6-F$_3$ | 2959, 2932, 1638, 1612, 1596, 1519, 1498, 1438, 1397, 1278, 1192, 1122, 1039, 999, 843 |
| I-68 | n-C$_6$H$_{13}$ | CH$_3$ | 2,4,6-F$_3$ | 2957, 2931, 1638, 1610, 1597, 1519, 1498, 1438, 1397, 1277, 1239, 1192, 1122, 1039, 1000 |
| I-69 | CH(CH$_3$)—(CH$_2$)$_2$CH$_3$ | CH$_3$ | 2,4,6-F$_3$ | 118 |
| I-70 | (CH$_2$)$_3$—CH(CH$_3$)$_2$ | CH$_3$ | 2,4,6-F$_3$ | 8.5 (s); 6.9 (m); 2.5 (s); 0.8 (d) |
| I-71 | (CH$_2$)$_2$CH(CH$_3$)C$_2$H$_5$ | CH$_3$ | 2,4,6-F$_3$ | 8.5 (s); 6.9 (m); 2.9 (m); 2.5 (s) |
| I-72 | CH$_2$CH(CH$_3$)(CH$_2$)$_2$—CH$_3$ | CH$_3$ | 2,4,6-F$_3$ | 8.5 (s); 6.9 (t); 3.0 (dd); 2.8 (dd); 2.5 (s) |
| I-73 | CH(CH$_3$)-n-C$_4$H$_9$ | CH$_3$ | 2,4,6-F$_3$ | 111 |
| I-74 | CH$_2$CH(C$_2$H$_5$)$_2$ | CH$_3$ | 2,4,6-F$_3$ | 90 |
| I-75 | CH(C$_2$H$_5$)-n-C$_3$H$_7$ | CH$_3$ | 2,4,6-F$_3$ | 110 |
| I-76 | 2-(CH$_3$)-c-C$_3$H$_4$ (Diastereomer 1) | CH$_3$ | 2,4,6-F$_3$ | 92 |
| I-77 | 2-(CH$_3$)-c-C$_3$H$_4$ (Diastereomer 2) | CH$_3$ | 2,4,6-F$_3$ | 125 |
| I-78 | c-C$_6$H$_{11}$ | CH$_3$ | 2-F, 4-CH$_3$ | 176 |
| I-79 | CH=C(CH$_3$)$_2$ | CH$_3$ | 2,4,6-F$_3$ | 103 |
| I-80 | CH(CH$_3$)COCH$_3$ | CH$_3$ | 2,4,6-F$_3$ | 165 |
| I-81 | CH$_2$—CH=C(CH$_3$)$_2$ | CH$_3$ | 2,4,6-F$_3$ | 81 |
| I-82 | 4-CH$_3$-cylohex-3-en-1-yl | CH$_3$ | 2,4,6-F$_3$ | 178 |
| I-83 | c-C$_6$H$_{11}$ | CH$_3$ | 2,6-F$_2$, 4-CH=C(CH$_3$)$_2$ | 145 |
| I-84 | c-C$_6$H$_{11}$ | CH$_3$ | CO—NH$_2$ | 231 |
| I-85 | CH$_2$CH(CH$_3$)CH(CH$_3$)$_2$ | CH$_3$ | 2,4,6-F$_3$ | 2962, 1638, 1610, 1596, 1516, 1497, 1438, 1396, 1276, 1238, 1192, 1122, 1039, 999, 843 |
| I-86 | c-C$_6$H$_{11}$ | CH$_3$ | 2,6-F$_2$, 4-CH=CH—CH(OCH$_3$)$_2$ | 8.45 (s); 7.1 (d); 6.75 (d); 6.3 (dd); 5.05 (d); 3.45 (s); 2.4 (s) |
| I-87 | c-C$_6$H$_{11}$ | CH$_3$ | 2,6-F$_2$, 4-OCN | 182 |
| I-88 | c-C$_6$H$_{11}$ | CH$_3$ | 2,6-F$_2$, 4-COCH$_3$ | 170 |
| I-89 | c-C$_6$H$_{11}$ | CH$_3$ | 2,6-F$_2$, 4-C(=NOCH$_3$)CH$_3$ | 2931, 1936, 1607, 1559, 1508, 1498, 1449, 1416, 1352, 1274, 1237, 1057, 1037, 873, 660 |
| I-90 | c-C$_6$H$_{11}$ | CH$_3$ | 2,6-F$_2$, 4-C(=NOC$_2$H$_5$)CH$_3$ | 2932, 1607, 1557, 1509, 1497, 1453, 1443, 1417, 1351, 1279, 1049, 1036, 1003, 877, 660 |
| I-91 | C(CH$_3$)=NOCH$_3$ | CH$_3$ | 2-Cl, 6-F | 117 |

TABLE I-continued

Compounds of the formula I

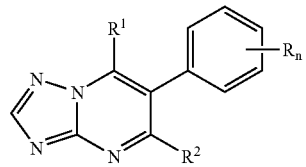

| No. | R¹ | R² | R$_n$ | Physical data (m.p.[° C.], IR[cm$^{-1}$], $^1$H-NMR[ppm]) |
|---|---|---|---|---|
| I-92 | C(CH$_3$)=NO-n-C$_4$H$_9$ | CH$_3$ | 2-Cl, 6-F | 2960, 2933, 1601, 1525, 1469, 1448, 1273, 1248, 1238, 1066, 1033, 893, 879, 785, 657 |
| I-93 | C(CH$_3$)=NO-n-C$_3$H$_7$ | CH$_3$ | 2-Cl, 6-F | 100 |
| I-94 | C(CH$_3$)=NOC$_2$H$_5$ | CH$_3$ | 2-Cl, 6-F | 94 |

Examples of the Activity Against Harmful Fungi

The fungicidal activity of the compounds of the formula I was demonstrated by the following experiments:

The active compounds, separately or together, were formulated as a 10% strength emulsion in a mixture of 70% by weight of cyclohexanone, 20% by weight of Nekanil® LN (Lutensol® AP6, wetting agent based on ethoxylated alkylphenols having emulsifying and dispersing action) and 10% by weight of Wettol®EM (nonionic emulsifier based on ethoxylated castor oil) and diluted with water to the desired concentration.

The compounds A to F known from WO-A 99/41255 served as comparative active compounds:

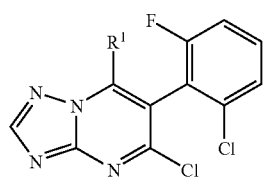

| No. | known from | R¹ |
|---|---|---|
| A | WO-A 99/41255, No.2c | 4-CH$_3$-c-C$_6$H$_{10}$ |
| B | WO-A 99/41255, No.26 | CH$_2$CH(CH$_3$)$_2$ |
| C | WO-A 99/41255, No.27 | CH(CH$_3$)$_2$ |
| D | WO-A 99/41255, No.29 | c-C$_5$H$_9$ |
| E | WO-A 99/41255, No.30 | c-C$_7$H$_{13}$ |
| F | WO-A 99/41255, No.31 | C$_6$H$_5$ |

Use Example 1

Activity Against *Aternaria solani* on Tomatoes

The leaves of potted plants of the cultivar "Große Fleischtomate St. Pierre" were sprayed to runoff point with an aqueous suspension which had been prepared from a stock solution made of 10% of active compound. 63% of cyclohexanone and 27% of emulsifier. The following day, the leaves were infected with an aqueous zoospore suspension of *Alternaria solani* in a 2% biomalt solution having a density of 0.17×10$^6$ spores/ml. The plants were then placed in a water-vapor-saturated chamber at 20-22° C. After 5 days, the foliar blight on the untreated but infected control plants had developed to such an extent that the infection could be determined visually in %.

In this test, the plants which had been treated with 63 ppm of the active compounds I-3 to I-8, I-11 to I-15, I-18, I-20, I-22, I-23, I-25, I-26, I-28 to I-32, I-35 to I-37, I-40, I-41, I-42, I-44, I-47, I-48, I-50 to I-54, I-56, I-58, I-59, I-61, I-62, I-64 and I-67 to I-74 of Table 1 showed an infection of at most 10%, whereas the plants which had been treated with 63 ppm of the comparative active compounds C and D showed an infection of at least 80% and the untreated plants an infection of 100%.

Use Example 2

Protective Activity Against Mildew of Cucumbers

Leaves of cucumber seedlings of the cultivar "Chinesische Schlange" which had been grown in pots were, at the cotyledon stage, sprayed to runoff point with an aqueous preparation of active compound which had been prepared using a stock solution made of 10% of active compound, 63% of cyclohexanone and 27% of emulsifier. 20 hours after the spray coating had dried on, the plants were inoculated with an aqueous spore suspension of mildew of cucumbers (*Sphaerotheca fuliginea*). The plants were then cultivated in a greenhouse at 20-24° C. and 60-80% relative atmospheric humidity for 7 days. The extent of the mildew development was then determined visually in % infection of the cotyledon area.

In this test, the plants which had been treated with 63 ppm of the active compounds I-3 to I-9, I-11 to I-15, I-17, I-18, I-20, I-22, I-23, I-25, I-26, I-28 to I-32, I-34, I-35, I-37, I-38, I-40, I-41, I-43, I-46, I-47, I-52, I-53, I-58, I-63, I-64, I-66 to I-75, I-93 and I-94 of Table I showed no infection or an infection of at most 10%, whereas the plants which had been treated with 63 ppm of the comparative active compounds A to F showed an infection of at least 60% and the untreated plants an infection of 100%.

Use Example 3

Protective Activity Against Net Blotch of Barley (*Pyrenophora teres*)

Leaves of barley seedlings of the cultivar "Igri" which had been grown in pots were sprayed to runoff point with an aqueous preparation of active compound which had been prepared from a stock solution made of 10% of active compound, 63% of cyclohexanone and 27% of emulsifier and were inoculated 24 hours after the spray coating had dried on with an aqueous spore suspension of *Pyrenophora teres*, the net blotch pathogen. The test plants were then placed in a greenhouse at 20-24° C. and 95-100% relative atmospheric humidity. After 6 days, the extent of the development of the disease was determined visually in % infection of the entire leaf area.

In this test, the plants which had been treated with 63 ppm of the active compounds I-3 to I-8, I-11, I-12, I-14, I-15, I-18, I-22, I-23, I-25, I-26, I-28 to I-32, I-35, I-36, I-37, I-40 to I-44, I-47, I-50 to I-53, I-58, I-61 to I-64, I-66 to I-74 and I-77 of Table I showed an infection of at most 20%, whereas the plants which had been treated with 63 ppm of the comparative active compounds B, D and F showed an infection of at least 60% and the untreated plants an infection of 100%.

We claim:

1. A triazolopyrimidine of the formula I

I 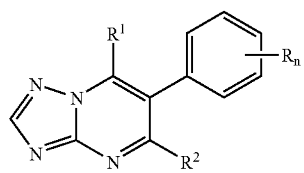 wherein:

n is 0 or an integer from 1 to 5;

R is halogen, cyano, hydroxy, OCN, $C_1$-$C_8$-alkyl, $C_2$-$C_{10}$-alkenyl, $C_2$-$C_{10}$-alkynyl, $C_1$-$C_6$-haloalkyl, $C_2$-$C_{10}$-haloalkenyl, $C_1$-$C_6$-alkoxy, $C_2$-$C_{10}$-alkenyloxy, $C_2$-$C_{10}$-alkynyloxy, $C_1$-$C_6$-haloalkoxy, $C_3$-$C_6$-cycloalkyl, $C_3$-$C_6$-cycloalkenyl, $C_3$-$C_6$-cycloalkoxy, $C_1$-$C_8$-alkoxycarbonyl, $C_2$-$C_{10}$-alkenyloxycarbonyl, $C_2$-$C_{10}$-alkynyloxycarbonyl, aminocarbonyl, $C_1$-$C_8$-alkylaminocarbonyl, di-($C_1$-$C_8$) alkylaminocarbonyl, $C_1$-$C_8$-alkoximinoalkyl, $C_2$-$C_{10}$-alkenyloximinocarbonyl, $C_2$-$C_6$-alkenyloximino $C_1$-$C_6$-alkyl, $C_2$-$C_{10}$-alkynyloximinoalkyl, $C_1$-$C_8$-alkylcarbonyl, $C_2$-$C_{10}$-alkenylcarbonyl, $C_2$-$C_{10}$-alkynylcarbonyl, $C_3$-$C_6$-cycloalkylcarbonyl, or a five- to ten-membered saturated, partially unsaturated or aromatic heterocycle which contains one to four heteroatoms from the group consisting of O, N and S;

$R^1$ is $C_3$-$C_8$-alkyl, $C_2$-$C_{10}$-alkenyl, $C_2$-$C_{10}$-alkynyl, $C_3$-$C_6$-cycloalkyl, $C_3$-$C_6$-cycloalkenyl, phenyl or naphthyl, where R and/or $R^1$ may be partially or fully halogenated or may be substituted by one to four identical or different groups $R^a$:

$R^a$ is halogen, cyano, nitro, hydroxyl, $C_1$-$C_8$-alkyl, $C_1$-$C_6$-haloalkyl, $C_1$-$C_6$-alkylcarbonyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_2$-$C_6$-alkenyl, $C_2$-$C_6$-alkenyloxy, $C_3$-$C_6$-alkynyloxy, $C_3$-$C_6$-cycloalkyl, $C_1$-$C_8$-alkoximino, $C_2$-$C_{10}$-alkenyloximino, $C_2$-$C_{10}$-alkynyloximino, aryl $C_1$-$C_8$-alkyloximino, $C_2$-$C_{10}$-alkynyl, $C_2$-$C_{10}$-alkenyloxycarbonyl, $C_2$-$C_{10}$-alkynyloxycarbonyl, phenyl, naphthyl, a five- to ten-membered saturated, partially unsaturated or aromatic heterocycle which contains one to four heteroatoms from the group consisting of O, N and S, where these aliphatic, alicyclic or aromatic groups may be partially or fully halogenated or may carry one to three groups $R^b$:

$R^b$ is halogen, cyano, nitro, hydroxyl, mercapto, amino, carboxyl, aminocarbonyl, aminothiocarbonyl, alkyl, haloalkyl, alkenyl, alkenyloxy, $C_2$-$C_6$ alkynyl alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;

and/or one to three of the following radicals:

cycloalkyl, cycloalkoxy, heterocyclyl, heterocyclyloxy, where the cyclic systems contain 3 to 10 ring members;

aryl, aryloxy, arylthio, aryl-$C_1$-$C_6$-alkoxy, aryl-$C_1$-$C_6$-alkyl, hetaryl, hetaryloxy, hetarylthio, where the cyclic systems may be partially or fully halogenated or substituted by alkyl or haloalkyl groups; and $R^2$ is $C_1$-$C_4$-alkyl, $C_2$-$C_4$-alkenyl or $C_2$-$C_4$-alkynyl, which may be substituted by halogen, cyano, nitro, $C_1$-$C_2$-alkoxy or $C_1$-$C_4$-alkoxycarbonyl.

2. A triazolopyrimidine of formula I as claimed in claim 1, wherein:

n is 0 or an integer from 1 to 5;

R is halogen, cyano, $C_1$-$C_6$-alkyl, $C_2$-$C_{10}$-alkenyl, $C_2$-$C_{10}$-alkynyl, $C_1$-$C_6$-haloalkyl, $C_2$-$C_{10}$-haloalkenyl, $C_1$-$C_6$-alkoxy, $C_2$-$C_{10}$-alkenyloxy, $C_2$-$C_{10}$-alkynyloxy, $C_1$-$C_6$-haloalkoxy, $C_3$-$C_6$-cycloalkyl, $C_3$-$C_6$-cycloalkenyl, $C_3$-$C_6$-cycloalkoxy or a five- to ten-membered saturated, partially unsaturated or aromatic heterocycle which contains one to four heteroatoms from the group consisting of O, N and S;

$R^1$ is $C_3$-$C_8$-alkyl, $C_2C_{10}$-alkenyl, $C_2$-$C_{10}$-alkynyl, $C_3$-$C_6$-cycloalkyl, $C_3$-$C_6$-cycloalkenyl, phenyl or naphthyl, where $R^1$ may be partially or fully halogenated or may be substituted by one to four identical or different groups $R^a$:

$R^a$ is halogen, cyano, nitro, hydroxyl, $C_1$-$C_6$-alkyl, $C_1$-$C_6$-haloalkyl, $C_1$-$C_6$-alkylcarbonyl, $C_3$-$C_6$-cycloalkyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_2$-$C_6$-alkenyl, $C_2$-$C_6$-alkenyloxy, $C_3$-$C_6$-alkynyloxy, $C_3$-$C_6$-cycloalkyl, phenyl, naphthyl, a five- to ten-membered saturated, partially unsaturated or aromatic heterocycle which contains one to four heteroatoms from the group consisting of O, N and S, where these aliphatic, alicyclic or aromatic groups may be partially or fully halogenated or may carry one to three groups $R^b$, and $R^2$ is $C_1$-$C_4$-alkyl which may be substituted by halogen, cyano, nitro or $C_1$-$C_2$-alkoxy.

3. A triazolopyrimidine of the formula I as claimed in claim 1, wherein:

n is an integer from 1 to 3;

R is fluorine, chlorine, bromine, cyano, $C_1$-$C_6$-alkyl, $C_1$-$C_6$-alkoxy, $C_1$-$C_6$-alkoxycarbonyl, $C_1$-$C_6$-alkylcarbonyl, $C_1$-$C_6$-alkoximino $C_1$-$C_6$-alkyl, $C_2$-$C_6$-alkenyloximino $C_1$-$C_6$-alkyl, $C_2$-$C_6$-alkynyloximino $C_1$-$C_6$-alkyl;

$R^1$ is $C_3$-$C_8$-alkyl, $C_3C_8$-alkenyl, $C_3$-$C_8$-alkynyl, $C_3$-$C_6$-cycloalkyl, $C_5$-$C_6$-cycloalkenyl;

$R^a$ is halogen, cyano, $C_1$-$C_6$-alkyl, $C_2$-$C_6$-alkenyl, $C_2$-$C_6$-alkynyl, $C_1$-$C_6$-alkoxy, $C_1$-$C_6$-alkoxycarbonyl, $C_1$-$C_6$-alkoximino, $C_2$-$C_6$-alkenyloximino, $C_2$-$C_6$-alkynyloximino;

$R^b$ is halogen, cyano, $C_1$-$C_6$-alkyl, $C_2$-$C_6$-alkenyl, $C_2$-$C_6$-alkynyl, $C_1$-$C_6$-alkoxy;

$R^2$ is $C_1$-$C_4$-alkyl which may be substituted by halogen.

4. A process for preparing compounds of the formula I as claimed in claim 1 by reacting 5-aminotriazole of the formula II

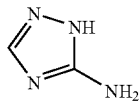

II with dicarbonyl compounds of the formula III

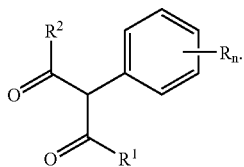

III

5. A process for preparing compounds of the formula I'

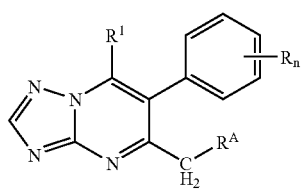

I' where n, R and $R^1$ are as defined in claim 1 and $R^A$ is hydrogen or $C_1$-$C_3$-alkyl which may be substituted as claimed in claim 1, by reacting halogen compounds of the formula IV

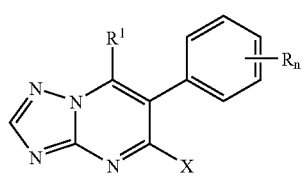

IV in which X is halogen with substituted malonic acid esters of the formula V

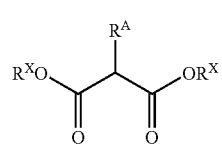

V in which $R^X$ is $C_1$-$C_4$-alkyl, allyl, phenyl or benzyl to give compounds of the formula VI,

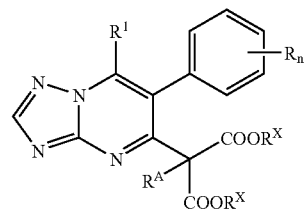

VI followed by hydrolysis of VI to give the acid VIa and decarboxylation of VIa

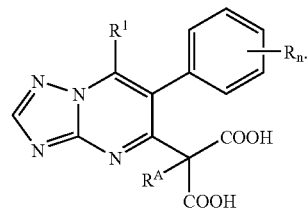

VIa

6. A composition suitable for controlling harmful fungi, which composition comprises a solid or liquid carrier and a compound of the formula I

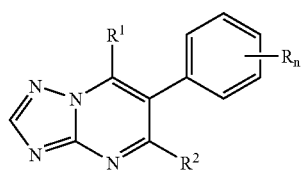

I wherein:

n is 0 or an integer from 1 to 5;

R is halogen, cyano, hydroxy, cyanato OCN, $C_1$-$C_8$-alkyl, $C_2$-$C_{10}$-alkenyl, $C_2$-$C_{10}$-alkynyl, $C_1$-$C_6$-haloalkyl, $C_2$-$C_{10}$-haloalkenyl, $C_1$-$C_6$-alkoxy, $C_2$-$C_{10}$-alkenyloxy, $C_2$-$C_{10}$-alkynyloxy, $C_1$-$C_6$-haloalkoxy, $C_3$-$C_6$-cycloalkyl, $C_3$-$C_6$-cycloalkenyl, $C_3$-$C_6$-cycloalkoxy, $C_1$-$C_8$-alkoxycarbonyl, $C_2$-$C_{10}$-alkenyloxycarbonyl, $C_2$-$C_{10}$-alkynyloxycarbonyl, aminocarbonyl, $C_1$-$C_8$-alkylaminocarbonyl, di ($C_1$-$C_8$) alkylaminocarbonyl, $C_1$-$C_8$-alkoximinoalkyl, $C_2$-$C_{10}$-alkenyloximinocarbonyl, $C_2$-$C_{10}$-alkynyloximinoalkyl, $C_1$-$C_8$-alkylcarbonyl, $C_2$-$C_{10}$-alkenylcarbonyl, $C_2$-$C_{10}$-alkynylcarbonyl, $C_3$-$C_6$-cycloalkylcarbonyl, or a five- to ten-membered saturated, partially unsaturated or aromatic heterocycle which contains one to four heteroatoms from the group consisting of O, N and S;

$R^1$ is $C_1$-$C_{10}$-alkyl, $C_2$-$C_{10}$-alkenyl, $C_2$-$C_{10}$-alkynyl, $C_3$-$C_{12}$-cycloalkyl, $C_3$-$C_{10}$-cycloalkenyl, phenyl or naphthyl, where R and/or $R^1$ may be partially or fully halogenated or may be substituted by one to four identical or different groups $R^a$:

$R^a$ is halogen, cyano, nitro, hydroxyl, $C_1$-$C_6$-alkyl, $C_1$-$C_6$-haloalkyl, $C_1$-$C_6$-alkylcarbonyl, $C_3$-$C_8$-cycloalkyl, $C_1$-$C_6$-alkoxy, $C_1$-$C_6$-haloalkoxy, $C_1$-$C_6$-alkoxycarbonyl, $C_1$-$C_6$-alkylthio, $C_1$-$C_8$-alkylamino, di-$C_1$-$C_6$-alkylamino, $C_2$-$C_2$-alkenyl, $C_2$-$C_6$-alkenyloxy, $C_3$-$C_8$-alkynyloxy, $C_3$-$C_6$-cycloalkyl, $C_1$-$C_8$-alkoximino, $C_2$-$C_{10}$-alkenyloximino, $C_2$-$C_{10}$-alkynyloximino, aryl $C_1$-$C_8$-alkyloximino, $C_2$-$C_{10}$-alkynyl, $C_2$-$C_{10}$-alkenyloxycarbonyl, $C_2$-$C_{10}$-alkynyloxycarbonyl, phenyl, naphthyl, a five- to ten-membered saturated, partially unsaturated or aromatic heterocycle which contains one to four heteroatoms from the group consisting of O, N and S, where these aliphatic, alicyclic or aromatic groups may be partially or fully halogenated or may carry one to three groups $R^b$:

$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;

and/or one to three of the following radicals:

cycloalkyl, cycloalkoxy, heterocyclyl, heterocyclyloxy, where the cyclic systems contain 3 to 10 ring members;

aryl, aryloxy, arylthio, aryl-$C_1$-$C_6$-alkoxy, aryl-$C_1$-$C_6$-alkyl, hetaryl, hetaryloxy, hetarylthio, where the cyclic systems may be partially or fully halogenated or substituted by alkyl or haloalkyl groups; and $R^2$ is $C_1$-$C_4$-alkyl, $C_2$-$C_4$-alkenyl or $C_2$-$C_4$-alkynyl, which may be substituted by halogen, cyano, nitro, $C_1$-$C_2$-alkoxy or $C_1$-$C_4$-alkoxycarbonyl.

7. A method for controlling harmful fungi, which comprises treating the fungi or the materials, plants, the soil or the seeds to be protected against fungal attack with an effective amount of a compound of the formula I

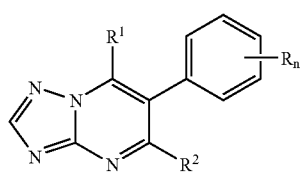

I wherein:
n is 0 or an integer from 1 to 5;
R is halogen, cyano, hydroxy, cyanato OCN, $C_1$-$C_8$-alkyl, $C_2$-$C_{10}$-alkenyl, $C_2$-$C_{10}$-alkynyl, $C_1$-$C_6$-haloalkyl, $C_2$-$C_{10}$-haloalkenyl, $C_1$-$C_6$-alkoxy, $C_2$-$C_{10}$-alkenyloxy, $C_2$-$C_{10}$-alkynyloxy, $C_1$-$C_6$-haloalkoxy, $C_3$-$C_6$-cycloalkyl, $C_3$-$C_6$-cycloalkenyl, $C_3$-$C_6$-cycloalkoxy, $C_1$-$C_8$-alkoxycarbonyl, $C_2$-$C_{10}$-alkenyloxycarbonyl, $C_2$-$C_{10}$-alkynyloxycarbonyl, aminocarbonyl, $C_1$-$C_8$-alkylaminocarbonyl, di-($C_1$-$C_8$) alkylaminocarbonyl, $C_1$-$C_8$-alkoximinoalkyl, $C_2$-$C_{10}$-alkenyloximinocarbonyl, $C_2$-$C_{10}$-alkynyloximinoalkyl, $C_1$-$C_8$-alkylcarbonyl, $C_2$-$C_{10}$-alkenylcarbonyl, $C_2$-$C_{10}$-alkynylcarbonyl, $C_3$-$C_6$-cycloalkylcarbonyl, or a five- to ten-membered saturated, partially unsaturated or aromatic heterocycle which contains one to four heteroatoms from the group consisting of O, N and S;

$R^1$ is $C_1$-$C_{10}$-alkyl, $C_2$-$C_{10}$-alkenyl, $C_2$-$C_{10}$-alkynyl, $C_3$-$C_{12}$-cycloalkyl, $C_3$-$C_{10}$-cycloalkenyl, phenyl or naphthyl, where R and/or $R^1$ may be partially or fully halogenated or may be substituted by one to four identical or different groups $R^a$:

$R^a$ is halogen, cyano, nitro, hydroxyl, $C_1$-$C_6$-alkyl, $C_1$-$C_6$-haloalkyl, $C_1$-$C_6$-alkylcarbonyl, $C_3$-$C_6$-cycloalkyl, $C_1$-$C_6$-alkoxy, $C_1$-$C_8$-haloalkoxy, $C_1$-$C_6$-alkoxycarbonyl, $C_1$-$C_6$-alkylthio, $C_1$-$C_6$-alkylamino, di-$C_1$-$C_6$-alkylamino, $C_2$-$C_6$-alkenyl, $C_2$-$C_6$-alkenyloxy, $C_3$-$C_6$-alkynyloxy, $C_3$-$C_6$-cycloalkyl, $C_1$-$C_8$-alkoximino, $C_2$-$C_{10}$-alkenyloximino, $C_2$-$C_{10}$-alkynyloximino, aryl $C_1$-$C_8$-alkyloximino, $C_2$-$C_{10}$-alkynyl, $C_2$-$C_{10}$-alkenyloxycarbonyl, $C_2$-$C_{10}$-alkynyloxycarbonyl, phenyl, naphthyl, a five- to ten-membered saturated, partially unsaturated or aromatic heterocycle which contains one to four heteroatoms from the group consisting of O, N and S, where these aliphatic, alicyclic or aromatic groups may be partially or fully halogenated or may carry one to three groups $R^b$:

$R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;

and/or one to three of the following radicals:

cycloalkyl, cycloalkoxy, heterocyclyl, heterocyclyloxy, where the cyclic systems contain 3 to 10 ring members;

aryl, aryloxy, arylthio, aryl-$C_1$-$C_6$-alkoxy, aryl-$C_1$-$C_6$-alkyl, hetaryl, hetaryloxy, hetarylthio, where the cyclic systems may be partially or fully halogenated or substituted by alkyl or haloalkyl groups; and $R^2$ is $C_1$-$C_4$-alkyl, $C_2$-$C_4$-alkenyl or $C_2$-$C_4$-alkynyl, which may be substituted by halogen, cyano, nitro, $C_1$-$C_2$-alkoxy or $C_1$-$C_4$-alkoxycarbonyl.

8. The triazolopyrimidine of claim 1 wherein $R^b$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;

and/or one to three of the following radicals:
cycloalkyl, cycloalkoxy, heterocyclyl, heterocyclyloxy, where the cyclic systems contain 3 to 10 ring members;
aryl, aryloxy, arylthio, aryl-$C_1$-$C_6$-alkoxy, aryl-$C_1$-$C_6$-alkyl, hetaryl, hetaryloxy, hetarylthio, where the aryl radicals contain 6 to 10 ring members and the hetaryl radicals 5 or 6 ring members, where the cyclic systems may be partially or fully halogenated or substituted by alkyl or haloalkyl groups.

9. The composition of claim 6 wherein
$R^2$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;
and/or one to three of the following radicals:
cycloalkyl, cycloalkoxy, heterocyclyl, heterocyclyloxy, where the cyclic systems contain 3 to 10 ring members;
aryl, aryloxy, arylthio, aryl-$C_1$-$C_6$-alkoxy, aryl-$C_1$-$C_6$-alkyl, hetaryl, hetaryloxy, hetarylthio, where the aryl radicals contain 6 to 10 ring members and the hetaryl radicals 5 or 6 ring members, where the cyclic systems may be partially or fully halogenated or substituted by alkyl or haloalkyl groups.

10. The method of claim 7 wherein Rb is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the alkenyl or alkynyl groups mentioned in these radicals contain 2 to 8 carbon atoms;
and/or one to three of the following radicals:
cycloalkyl, cycloalkoxy, heterocyclyl, heterocyclyloxy, where the cyclic systems contain 3 to 10 ring members;
aryl, aryloxy, arylthio, aryl-$C_1$-$C_6$-alkoxy, aryl-$C_1$-$C_6$-alkyl, hetaryl, hetaryloxy, hetarylthio, where the aryl radicals contain 6 to 10 ring members and the hetaryl radicals 5 or 6 ring members, where the cyclic systems may be partially or fully halogenated or substituted by alkyl or haloalkyl groups.

* * * * *

UNITED STATES PATENT AND TRADEMARK OFFICE
CERTIFICATE OF CORRECTION

PATENT NO. : 7,300,908 B2
APPLICATION NO. : 10/482216
DATED : November 27, 2007
INVENTOR(S) : Müller et al.

It is certified that error appears in the above-identified patent and that said Letters Patent is hereby corrected as shown below:

Claim 1, col. 31, line 58: "$C_1$-$C_8$-alkyl" should read --$C_1$-$C_6$-alkyl--

Claim 1, col. 32, lines 9 - 10: "$C_2$-$C_6$ alkynyl alkynyloxy" should read --$C_2$-$C_6$-alkynyl, alkynyloxy--

Claim 2, col. 32, line 40: "$C_2C_{10}$-alkenyl" should read --$C_2$-$C_{10}$-alkenyl--

Claim 3, col. 33, line 1: "$C_3C_8$-alkenyl" should read --$C_3$-$C_8$-alkenyl--

Claim 6, col. 34, line 55: "cyanato OCN" should read --OCN--

Claim 6, col. 34, line 63: "di ($C_1$-$C_8$) alkylaminocarbonyl" should read --di-($C_1$-$C_8$)alkylaminocarbonyl--

Claim 6, col. 35, line 10: "$C_3$-$C_8$-cycloalkyl" should read --$C_3$-$C_6$-cycloalkyl--

Claim 6, col. 35, line 12: "$C_1$-$C_8$-alkylamino" should read --$C_1$-$C_6$-alkylamino--

Claim 6, col. 35, line 13: "$C_2$-$C_2$-alkenyl" should read --$C_2$-$C_6$-alkenyl--

Claim 6, col. 35, lines 13 - 14: "$C_3$-$C_8$-alkynyloxy" should read --$C_3$-$C_6$-alkynyloxy--

Claim 7, col. 35, line 64: "cyanato OCN" should read --OCN--

UNITED STATES PATENT AND TRADEMARK OFFICE
CERTIFICATE OF CORRECTION

PATENT NO. : 7,300,908 B2
APPLICATION NO. : 10/482216
DATED : November 27, 2007
INVENTOR(S) : Müller et al.

It is certified that error appears in the above-identified patent and that said Letters Patent is hereby corrected as shown below:

Claim 7, col. 36, line 4: "di-$(C_1$-$C_8)$ alkylaminocarbonyl" should read --di-$(C_1$-$C_8)$alkylaminocarbonyl--

Claim 7, col. 36, line 19: "$C_1$-$C_8$-haloalkoxy" should read --$C_1$-$C_6$-haloalkoxy--

Claim 10, col. 38, line 5, "Rb" should read --$R^b$--

Signed and Sealed this

Fifteenth Day of April, 2008

JON W. DUDAS
*Director of the United States Patent and Trademark Office*